(12) United States Patent
Fujikura et al.

(10) Patent No.: US 7,129,381 B2
(45) Date of Patent: Oct. 31, 2006

(54) GLUCOPYRANOSYLOXYBENZYLBENZENE DERIVATIVES, MEDICINAL COMPOSITIONS CONTAINING THE SAME AND INTERMEDIATES IN THE PRODUCTION THEREOF

(75) Inventors: Hideki Fujikura, Nagano (JP); Toshihiro Nishimura, Nagano (JP); Nobuhiko Fushimi, Nagano (JP); Kazuya Tatani, Nagano (JP); Norihiko Kikuchi, Nagano (JP); Kenji Katsuno, Nagano (JP); Masayuki Isaji, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 10/978,413

(22) Filed: Nov. 2, 2004

(65) Prior Publication Data

US 2005/0059614 A1 Mar. 17, 2005

Related U.S. Application Data

(62) Division of application No. 10/432,905, filed as application No. PCT/JP01/10115 on Nov. 20, 2001, now Pat. No. 7,053,060.

(30) Foreign Application Priority Data

Nov. 30, 2000 (JP) ............................. 2000-366192
Dec. 14, 2000 (JP) ............................. 2000-380482

(51) Int. Cl.
C07C 15/00 (2006.01)
C07C 27/10 (2006.01)
C07C 33/18 (2006.01)
C07C 39/00 (2006.01)

(52) U.S. Cl. .................. 568/716; 568/300; 568/700; 568/715; 568/731; 568/732; 568/743; 568/744

(58) Field of Classification Search ............... 568/300, 568/700, 715, 716, 731, 732, 743, 744
See application file for complete search history.

(56) References Cited

U.S. PATENT DOCUMENTS

| 4,598,068 A | 7/1986 | Samreth et al. |
| 4,874,763 A * | 10/1989 | Hofmann et al. ........... 514/249 |
| 5,232,946 A | 8/1993 | Harnaus et al. |
| 5,424,406 A | 6/1995 | Tsjihara et al. |
| 5,731,292 A | 3/1998 | Tsjihara et al. |
| 6,683,056 B1 | 1/2004 | Washburn et al. |
| 2005/0065098 A1* | 3/2005 | Fujikura et al. ............... 514/23 |
| 2005/0075294 A1* | 4/2005 | Fujikura et al. ............... 514/25 |
| 2005/0080022 A1* | 4/2005 | Fujikura et al. ............... 514/25 |
| 2005/0113315 A1* | 5/2005 | Fujikura et al. ............... 514/25 |
| 2005/0137143 A1* | 6/2005 | Fujikura et al. ............... 514/23 |

FOREIGN PATENT DOCUMENTS

| DE | 37 40441 A1 | 6/1989 |
| EP | 598359 A1 | 5/1994 |
| JP | 5-296857 A | 11/1993 |
| JP | 9-241128 A | 9/1997 |
| WO | WO 01/68660 A | 9/2001 |
| WO | WO 01/74834 A1 | 10/2001 |

* cited by examiner

Primary Examiner—Shaojia Anna Jiang
Assistant Examiner—Traviss McIntosh
(74) Attorney, Agent, or Firm—Sughrue Mion, PLLC

(57) ABSTRACT

The present invention relates to glucopyranosyl-oxybenzyl-benzene derivatives represented by the general formula:

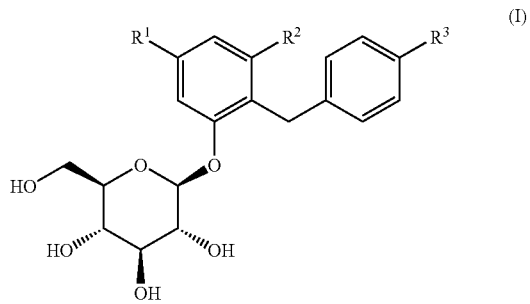

wherein $R^1$ represents a hydrogen atom, a hydroxy group, a substituted or unsubstituted amino group, a carbamoyl group, a substituted or unsubstituted(lower alkyl) group, a substituted or unsubstituted(lower alkoxy) group etc.; $R^2$ represents a hydrogen atom or a lower alkyl group; and $R^3$ represents a substituted or unsubstituted(lower alkyl) group, a substituted or unsubstituted(lower alkoxy) group, a substituted or unsubstituted(lower alkylthio) group etc., or pharmaceutically acceptable salts thereof, which have an inhibitory activity in human SGLT2 and are useful as agents for the prevention or treatment of a disease associated with hyperglycemia such as diabetes, diabetic complication or obesity, pharmaceutical compositions comprising the same and intermediates thereof.

1 Claim, No Drawings

```
                        SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 1
atggaggagc acacagaggc                                           20

<210> SEQ ID NO 2
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 2
ggcatagaag ccccagagga                                           20

<210> SEQ ID NO 3
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 3
aacctcgaga tggaggagca cacagaggc                                 29

<210> SEQ ID NO 4
<211> LENGTH: 29
<212> TYPE: DNA
<213> ORGANISM: Artificial Sequence
<220> FEATURE:
<223> OTHER INFORMATION: Synthetic DNA primer
```

```
<400> SEQUENCE: 4
aacaagcttg gcatagaagc cccagagga                                        29

<210> SEQ ID NO 5
<211> LENGTH: 25
<212> TYPE: PRT
<213> ORGANISM: Artificial Sequence
<220> FEATURE:
<223> OTHER INFORMATION: Peptide fused to the carboxyl terminal alanine
      residue of human SGLT2

<400> SEQUENCE: 5

Lys Leu Gly Pro Glu Gln Lys Leu Ile Ser Glu Glu Asp Leu Asn Ser
1               5                   10                  15

Ala Val Asp His His His His His His
            20                  25
```

GLUCOPYRANOSYLOXYBENZYLBENZENE DERIVATIVES, MEDICINAL COMPOSITIONS CONTAINING THE SAME AND INTERMEDIATES IN THE PRODUCTION THEREOF

This is a divisional of application Ser. No. 10/432,905 filed Oct. 6, 2003 now U.S. Pat. No. 7,053,060 which is a national stage entry of PCT/JP01/10115 filed Nov. 20, 2001. The entire disclosure(s) of the prior application(s), application Ser. No. 10/432,905 is considered part of the disclosure of the accompanying divisional application and is hereby incorporated by reference.

TECHNICAL FIELD

The present invention relates to glucopyranosyloxybenzylbenzene derivatives or pharmaceutically acceptable salts thereof, which are useful as medicaments, pharmaceutical compositions comprising the same and intermediates thereof.

More particularly, the present invention relates to glucopyranosyloxybenzylbenzene derivatives or pharmaceutically acceptable salts thereof, which have an inhibitory activity in human SGLT2 and are useful as agents for the prevention or treatment of a disease associated with hyperglycemia such as diabetes, diabetic complication or obesity, pharmaceutical compositions comprising the same and intermediates thereof.

BACKGROUND ART

Diabetes is one of lifestyle-related diseases with the background of change of eating habit and lack of exercise. Hence, diet and exercise therapies are performed in patients with diabetes. Furthermore, when its sufficient control and continuous performance are difficult, drug treatment is simultaneously performed. Now, biguanides, sulfonylureas and agents for reducing insulin resistance have been employed as antidiabetic agents. However, biguanides and sulfonylureas show occasionally adverse effects such as lactic acidosis and hypoglysemia, respectively. In a case of using agents for reducing insulin resistance, adverse effects such as edema occasionally are observed, and it is also concerned for advancing obesity. Therefore, in order to solve these problems, it has been desired to develop antidiabetic agents having a new mechanism.

In recent years, development of new type antidiabetic agents has been progressing, which promote urinary glucose excretion and lower blood glucose level by preventing excess glucose reabsorption at the kidney (J. Clin. Invest., Vol. 79, pp. 1510–1515 (1987)). In addition, it is reported that SGLT2 (Na$^+$/glucose cotransporter 2) is present in the S1 segment of the kidney's proximal tubule and participates mainly in reabsorption of glucose filtrated through glomerular (J. Clin. Invest., Vol. 93, pp. 397–404 (1994)). Accordingly, inhibiting a human SGLT2 activity prevents reabsorption of excess glucose at the kidney, subsequently promotes excreting excess glucose though the urine, and normalizes blood glucose level. Therefore, fast development of antidiabetic agents, which have a potent inhibitory activity in human SGLT2 and have a new mechanism, has been desired. Furthermore, since such agents promote the excretion of excess glucose though the urine and consequently the glucose accumulation in the body is decreased, they are also expected to have a preventing effect on obesity.

DISCLOSURE OF THE INVENTION

The present inventors have studied earnestly to find compounds having an inhibitory activity in human SGLT2. As a result, it was found that certain glucopyranosyloxybenzylbenzene derivatives show an excellent inhibitory activity in human SGLT2 as mentioned below, thereby forming the basis of the present invention.

The present invention is to provide the following glucopyranosyloxybenzylbenzene derivatives and pharmaceutically acceptable salts thereof, which exert an inhibitory activity in human SGLT2 and show an excellent hypoglycemic effect by excreting excess glucose in the urine through preventing the reabsorption of excess glucose at the kidney, and pharmaceutical compositions comprising the same.

This is, the present invention relates to a glucopyranosyloxybenzylbenzene derivative represented by the general formula:

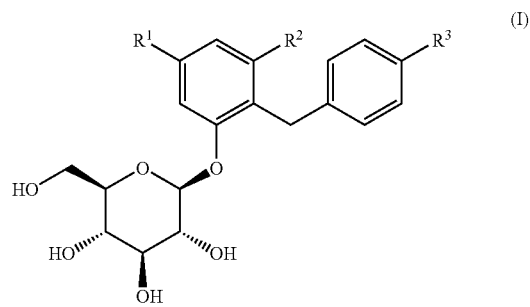

wherein $R^1$ represents a hydrogen atom, a hydroxy group, an amino group, a mono or di(lower alkyl)amino group, a carbamoyl group, a lower alkyl group, a lower alkoxy group, a hydroxy(lower alkyl) group, a hydroxy(lower alkoxy) group, a lower alkoxy-substituted (lower alkyl) group, a lower alkoxy-substituted (lower alkoxy) group, a carbamoyl (lower alkyl) group, a lower alkoxy-carbonyl-substituted (lower alkyl) group, a lower alkoxy-carbonyl-substituted (lower alkoxy) group, a carboxy(lower alkyl) group or a carboxy(lower alkoxy) group; $R^2$ represents a hydrogen atom or a lower alkyl group; and $R^3$ represents a lower alkyl group, a lower alkoxy group, a lower alkylthio group, a hydroxy(lower alkyl) group, a hydroxy(lower alkoxy) group, a hydroxy(lower alkylthio) group, a lower alkoxy-substituted (lower alkyl) group, a lower alkoxy-substituted (lower alkoxy) group, a lower alkoxy-substituted (lower alkylthio) group, a lower alkenyloxy group, an aralkyloxy group, a hydroxy(lower alkenyl) group, a carboxy group, a lower alkoxycarbonyl group, a cyano group, an aralkyloxy (lower alkyl) group, a cyano(lower alkyl) group, a carbamoyl group, a carbamoyl(lower alkyl) group, an amino group, a mono or di(lower alkyl)amino group, a lower alkoxycarbonyl-substituted (lower alkyl) group, a lower alkoxycarbonyl-substituted (lower alkoxy) group, a carboxy-(lower alkyl) group or a carboxy(lower alkoxy) group; with the proviso that $R^3$ does not represent a lower alkyl group, a lower alkoxy group, a lower alkylthio group, a hydroxy (lower alkyl) group, a hydroxy(lower alkoxy) group, a hydroxy (lower alkylthio) group, a lower alkoxy-substituted (lower alkyl) group, a lower alkoxy-substituted (lower alkoxy) group or a lower alkoxy-substituted (lower alkylthio) group when $R^1$ represents a hydrogen atom or a hydroxy(lower alkyl) group and $R^2$ represents a hydrogen atom, or a pharmaceutically acceptable salt thereof.

The present invention relates to a pharmaceutical composition comprising as an active ingredient a glucopyranosyloxybenzylbenzene derivative represented by the above general formula (I) or a pharmaceutically acceptable salt thereof.

The present invention relates to a human SGLT2 inhibitor comprising as an active ingredient a glucopyranosyloxybenzylbenzene derivative represented by the above general formula (I) or a pharmaceutically acceptable salt thereof.

The present invention relates to an agent for the prevention or treatment of a disease associated with hyperglycemia, which comprises as an active ingredient a glucopyranosyloxybenzylbenzene derivative represented by the above general formula (I) or a pharmaceutically acceptable salt thereof.

The present invention relates to a method for the prevention or treatment of a disease associated with hyperglycemia, which comprises administering an effect amount of a glucopyranosyloxybenzylbenzene derivative represented by the above general formula (I) or a pharmaceutically acceptable salt thereof.

The present invention relates to a use of a glucopyranosyloxybenzylbenzene derivative represented by the above general formula (I) or a pharmaceutically acceptable salt thereof for the manufacture of a pharmaceutical composition for the prevention or treatment of a disease associated with hyperglycemia.

In addition, the present invention relates to a benzylphenol derivative represented by the general formula:

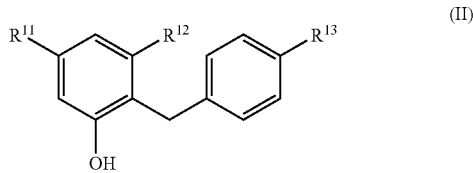

wherein $R^{11}$ represents a hydrogen atom, a protected hydroxy group, a protected amino group, a protected mono(lower alkyl)amino group, a di(lower alkyl)amino group, a carbamoyl group, a lower alkyl group, a lower alkoxy group, a protected hydroxy(lower alkyl) group, a protected hydroxy(lower alkoxy) group, a lower alkoxy-substituted (lower alkyl) group, a lower alkoxy-substituted (lower alkoxy) group, a carbamoyl (lower alkyl) group, a lower alkoxycarbonyl-substituted (lower alkyl) group, a lower alkoxycarbonyl-substituted (lower alkoxy) group, a carboxy-(lower alkyl) group or a carboxy(lower alkoxy) group; $R^{12}$ represents a hydrogen atom or a lower alkyl group; and $R^{13}$ represents a lower alkyl group, a lower alkoxy group, a lower alkylthio group, a protected hydroxy(lower alkyl) group, a protected hydroxy(lower alkoxy) group, a protected hydroxy-(lower alkylthio) group, a lower alkoxy-substituted (lower alkyl) group, a lower alkoxy-substituted (lower alkoxy) group, a lower alkoxy-substituted (lower alkylthio) group, a lower alkenyloxy group, an aralkyloxy group, a protected hydroxy(lower alkenyl) group, a carboxy group, a lower alkoxycarbonyl group, a cyano group, an aralkyloxy (lower alkyl) group, a cyano(lower alkyl) group, a carbamoyl group, a carbamoyl(lower alkyl) group, an protected amino group, a protected mono(lower alkyl)amino group, a di(lower alkyl)amino group, a lower alkoxy-carbonyl-substituted (lower alkyl) group, a lower alkoxy-carbonyl-substituted (lower alkoxy) group, a carboxy(lower alkyl) group or a carboxy(lower alkoxy) group; with the proviso that $R^{13}$ does not represent a lower alkyl group, a lower alkoxy group, a lower alkylthio group, a protected hydroxy(lower alkyl) group, a protected hydroxy(lower alkoxy) group, a protected hydroxy(lower alkylthio) group, a lower alkoxy-substituted (lower alkyl) group, a lower alkoxy-substituted (lower alkoxy) group or a lower alkoxy-substituted (lower alkylthio) group when $R^{11}$ represents a hydrogen atom or a protected hydroxy(lower alkyl) group and $R^{12}$ represents a hydrogen atom, or a salt thereof.

In the present invention, the term "lower alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "lower alkoxy group" means a straight-chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group or the like; and the term "lower alkylthio group" means a straight-chained or branched alkylthio group having 1 to 6 carbon atoms such as a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, a tert-pentylthio group, a hexylthio group or the like. The term "hydroxy(lower alkyl) group" means a straight-chained or branched hydroxyalkyl group having 1 to 6 carbon atoms such as a hydroxymethyl group, a 2-hydroxyethyl group, a 1-hydroxyethyl group, a 3-hydroxypropyl group, a 2-hydroxypropyl group, a 1-hydroxypropyl group, a 2-hydroxy-1-methylethyl group, a 4-hydroxybutyl group, a 3-hydroxybutyl group, a 2-hydroxybutyl group, a 1-hydroxybutyl group, a 5-hydroxypentyl group, a 4-hydroxypentyl group, a 3-hydroxypentyl group, a 2-hydroxypentyl group, a 1-hydroxypentyl group, a 6-hydroxyhexyl group, a 5-hydroxyhexyl group, a 4-hydroxyhexyl group, a 3-hydroxyhexyl group, a 2-hydroxyhexyl group, a 1-hydroxyhexyl group or the like; the term "hydroxy(lower alkoxy) group" means a straight-chained or branched hydroxyalkoxy group having 2 to 6 carbon atoms such as a 2-hydroxyethoxy group, a 3-hydroxypropoxy group, a 2-hydroxypropoxy group, a 2-hydroxy-1-methylethoxy group, a 4-hydroxybutoxy group, a 3-hydroxybutoxy group, a 2-hydroxybutoxy group, a 5-hydroxypentyloxy group, a 4-hydroxypentyloxy group, a 3-hydroxypentyloxy group, a 2-hydroxypentyloxy group, a 6-hydroxyhexyloxy group, a 5-hydroxyhexyloxy group, a 4-hydroxyhexyloxy group, a 3-hydroxyhexyloxy group, a 2-hydroxyhexyloxy group or the like; and the term "hydroxy(lower alkylthio) group" means a straight-chained or branched hydroxyalkylthio group having 2 to 6 carbon atoms such as an 2-hydroxyethylthio group, a 3-hydroxypropylthio group, a 2-hydroxypropylthio group, a 2-hydroxy-1-methylethylthio group, a 4-hydroxybutylthio group, a 3-hydroxybutylthio group, a 2-hydroxybutylthio group, a 5-hydroxypentylthio group, a 4-hydroxypentylthio group, a 3-hydroxypentylthio group, a 2-hydroxypentylthio group, a 6-hydroxyhexylthio group, a 5-hydroxyhexylthio group, a 4-hydroxyhexylthio group, a 3-hydroxyhexylthio group, a 2-hydroxyhexylthio group or the like. The term "lower alkoxy-substituted (lower alkyl) group" means the above lower alkyl group substituted by the above lower alkoxy group; the term "lower alkoxy-substituted (lower alkoxy) group" means the above lower alkoxy group substituted by the above lower alkoxy group; and the term "lower alkoxy-substituted (lower alkylthio) group" means the above lower alkylthio group substituted by the above lower alkoxy group. The term "lower alkenyloxy group" a straight-chained or branched alkenyloxy group having 2 to 6 carbon atoms such as an allyloxy group; the term "hydroxy (lower alkenyl) group" means a straight-chained or branched hydroxy-alkenyl group having 3 to 6 carbon atoms such as an 3-hydroxy-1-propenyl group; the term "aralkyloxy group" means the above lower alkoxy group substituted by an aryl group (e.g., a phenyl group, a naphthyl group and the like) such as a benzyloxy group; the term "aralkyloxy(lower alkyl) group" means the above lower alkyl group substituted by the above aralkyloxy group; the term "cyano(lower alkyl) group" means the above lower alkyl group substituted by a cyano group; the term "carbamoyl(lower alkyl) group" means the above lower alkyl group substituted by a carbamoyl group; and "mono or di(lower alkyl)amino group" means an amino group mono or disubstituted by the above lower alkyl group. The term "lower alkoxycarbonyl group" means a straight-chained or branched alkoxycarbonyl group having 2 to 7 carbon atoms such as a methoxycarbonyl group, an ethoxycarbonyl group, a propoxycarbonyl group, an isopropyloxycarbonyl group, a butoxycarbonyl group, an isobutyloxycarbonyl group, a sec-butoxycarbonyl group, a tert-butoxycarbonyl group, a pentyloxycarbonyl group, an isopentyloxycarbonyl group, a neopentyloxycarbonyl group, a tert-pentyloxycarbonyl group, a hexyloxycarbonyl group or the like; the term "lower alkoxy-carbonyl-substituted (lower alkyl) group" means the above lower alkyl group substituted by the above lower alkoxycarbonyl group; the term "lower alkoxycarbonyl-substituted (lower alkoxy) group" means the above lower alkoxy group substituted by the above lower alkoxycarbonyl group; and the term "carboxy(lower alkyl) group" means the above lower alkyl group substituted by a carboxy group; and the term "carboxy (lower alkoxy) group means the above lower alkoxy group substituted by a carboxy group.

The term "hydroxy-protective group" means a hydroxy-protective group used in general organic reactions such as a benzyl group, a methoxymethyl group, an acetyl group, a benzoyl group or the like. The term "amino-protective group" means an amino-protective group used in general organic reactions such as a benzyloxycarbonyl group, a tert-butoxycarbonyl group, a phthaloyl group, a benzyl group, an acetyl group or the like.

For example, the compounds represented by the above general formula (I) of the present invention can be prepared using a benzylphenol derivative represented by the above general formula (II) of the present invention according the following procedure:

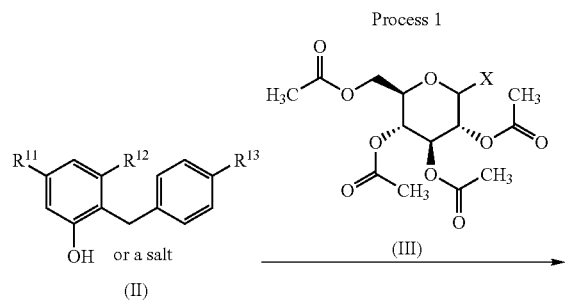

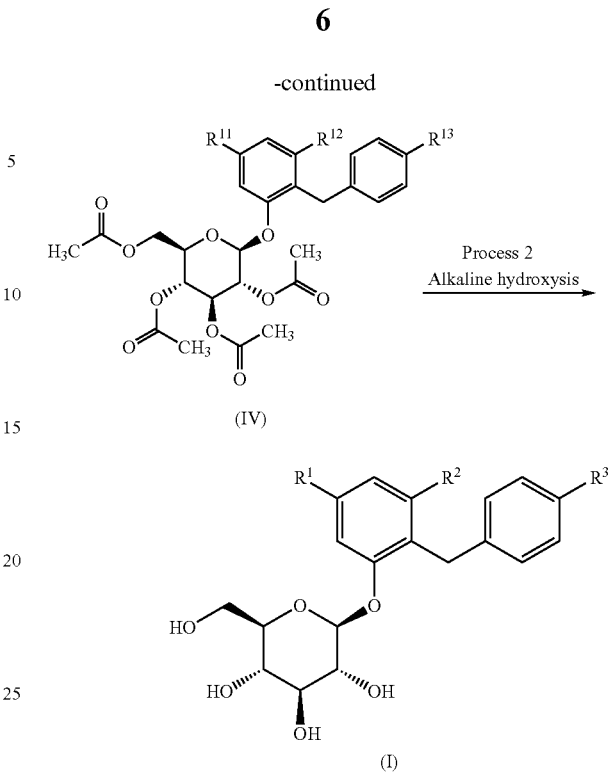

wherein X represents a leaving group such as a trichloroacetoimidoyloxy group, an acetoxy group, a bromine atom or a fluorine atom; and $R^1$, $R^2$, $R^3$, $R^{11}$, $R^{12}$ and $R^{13}$ have the same meanings as defined above.

Process 1

A glucoside represented by the above general formula (IV) can be prepared by subjecting a benzylphenol derivative represented by the above general formula (II) or a salt thereof to glycosidation using a glycosyl-donor represented by the above general formula (III) such as 2,3,4,6-tetra-O-acetyl-1-O-trichloroacetoimidoyl-α-D-glucopyranose, 2,3,4,6-tetra-O-acetyl-1-O-trichloroacetoimidoyl-β-D-glucopyranose, 1,2,3,4,6-penta-O-acetyl-β-D-glucopyranose, 2,3,4,6-tetra-O-acetyl-α-D-glucopyranosyl bromide and 2,3,4,6-tetra-O-acetyl-β-D-glucopyranosyl fluoride in the presence of an activating reagent such as boron trifluoride-diethyl ether complex, silver trifluoromethanesulfonate, tin (IV) chloride or trimethylsilyl trifluoromethanesulfonate in an inert solvent. As the solvent used, dichloromethane, toluene, acetonitrile, nitromethane, ethylacetate, diethylether, chloroform, a mixed solvent thereof and the like can be illustrated. The reaction temperature is usually from −30° C. to reflux temperature, and the reaction time is usually from 10 minutes to 1 day, varying based on a used starting material, solvent and reaction temperature. In addition, compounds wherein substituents $R^{11}$ and/or $R^{13}$ have a hydroxy-protective group or an amino-protective group can be used in the process 2 after removing appropriately the protective group in the usual way subsequent to reaction completion of this process.

Process 2

A compound (I) of the present invention can be prepared by subjecting a glucoside represented by the above general formula (IV) to alkaline hydrolysis to remove the hydroxy-protective groups. As the solvent used, water, methanol, ethanol, tetrahydrofuran, a mixed solvent thereof and the like can be illustrated, and as alkaline materials, sodium hydroxide, sodium methoxide, sodium ethoxide or the like can be used. The treatment temperature is usually from 0° C. to reflux temperature, and the treatment time is usually from 30 minutes to 6 hours, varying based on a used starting material, solvent and treatment temperature. In addition, compounds wherein substituents $R^{11}$ and/or $R^{13}$ have a hydroxy-protective group or an amino-protective group can be carried out by modifying the above treatment method appropriately in the usual way and can be derived into a desired compound (I) by removing the protective group in the usual way subsequent to reaction completion of this process.

For example, of the compounds represented by the above general formula (I) of the present invention, compounds represented by the following general formula (Ia) can be also prepared using a carboxylic acid derivative represented by the above general formula (V) according the following procedure:

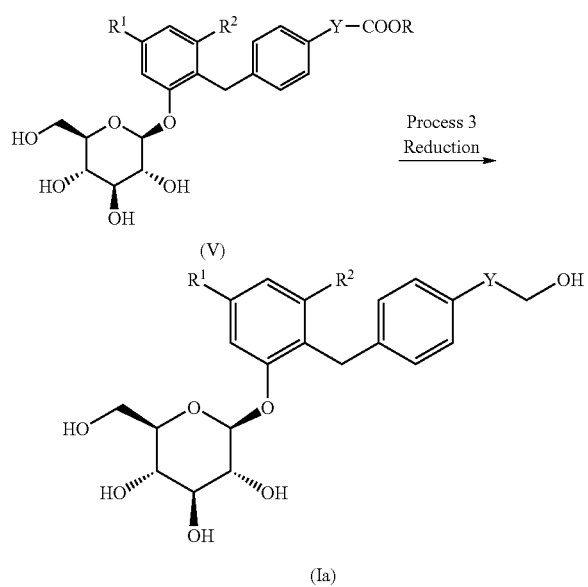

wherein Y represents a straight-chained or branched alkyl group having 1 to 5 carbon atoms or a straight-chained or branched alkenyl group having 2 to 5 carbon atoms; R represents a hydrogen atom or a lower alkyl group; and $R^1$ and $R^2$ have the same meanings as defined above.

Process 3

A compound represented by the above general formula (Ia) can be prepared by subjecting a carboxylic acid derivative represented by the above general formula (V) to reduction using a reducing agent such as lithium aluminium hydride, boran or lithium borohydride in a solvent such as tetrahydrofuran, diethyl ether, methanol, ethanol or a mixed solvent thereof. The reaction temperature is usually from 0° C. to reflux temperature, and the reaction time is usually from 30 minutes to 1 day, varying based on a used starting material, solvent and reaction temperature.

Furthermore, for example, of the compounds represented by the above general formula (I) of the present invention, compounds represented by the following general formula (Ib) can be also prepared using a phenol derivative represented by the above general formula (Ic) according the following procedure:

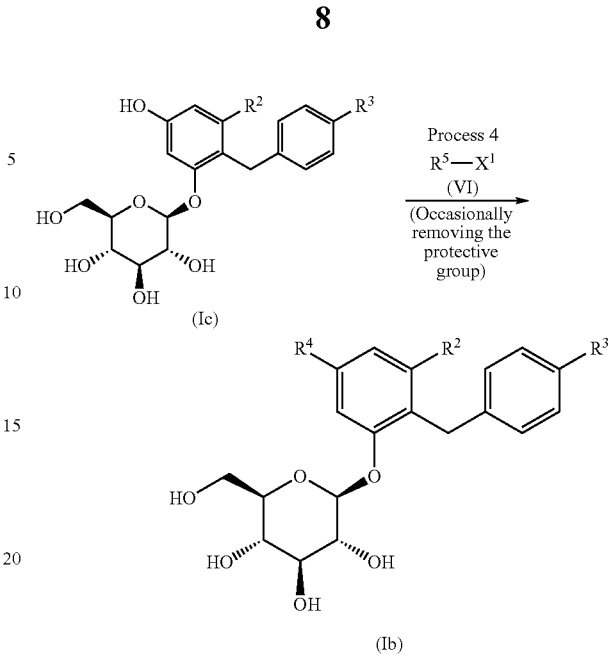

wherein $R^4$ represents a lower alkoxy group, a hydroxy (lower alkoxy) group, a lower alkoxy-substituted (lower alkoxy) group, a lower alkoxycarbonyl-substituted (lower alkoxy) group or a carboxy(lower alkoxy) group; $R^5$ represents a lower alkyl group, a protected hydroxy(lower alkyl) group, a lower alkoxy-substituted (lower alkyl) group or a lower alkoxycarbonyl-substituted (lower alkyl) group; $X^1$ represents a leaving group such as a chlorine atom, a bromine atom, an iodine atom, a mesyloxy group or tosyloxy group; and $R^2$ and $R^3$ have the same meanings as defined above.

Process 4

A compound represented by the above general formula (Ib) can be prepared by subjecting a phenol derivative represented by the above general formula (Ic) to O-alkylation using an alkylating agent represented by the above general formula (VI) in the presence of an alkaline material such as sodium hydride, potassium carbonate, cesium carbonate, potassium tert-butoxide, sodium hydroxide, potassium hydroxide or sodium hydrogen carbonate in a solvent such as tetrahydrofuran, N,N-dimethyl-formamide, dimethyl sulfoxide, acetonitrile or a mixed solvent thereof, and removing the protective group in the usual way as occasion demands. The reaction temperature is usually from 0° C. to reflux temperature, and the reaction time is usually from 30 minutes to 1 day, varying based on a used starting material, solvent and reaction temperature.

Of the compounds represented by the above general formula (IV), compounds wherein $R^{11}$ represents a protected mono(lower alkyl)amino group can be prepared by allowing a corresponding compound wherein $R^{11}$ represents a protected amino group to react with an appropriate alkylating agent such as a lower alkyl halide, a mesylate compound or a tosylate compound in the presence of an alkaline material such as sodium hydride or potassium carbonate in a solvent such as tetrahydrofuran, N,N-dimethyl-formamide, dimethyl sulfoxide or a mixed solvent thereof.

For example, the compounds represented by the above general formula (II) of the present invention which are used as starting materials in the aforementioned production process and salts thereof can be prepared according to the following procedure:

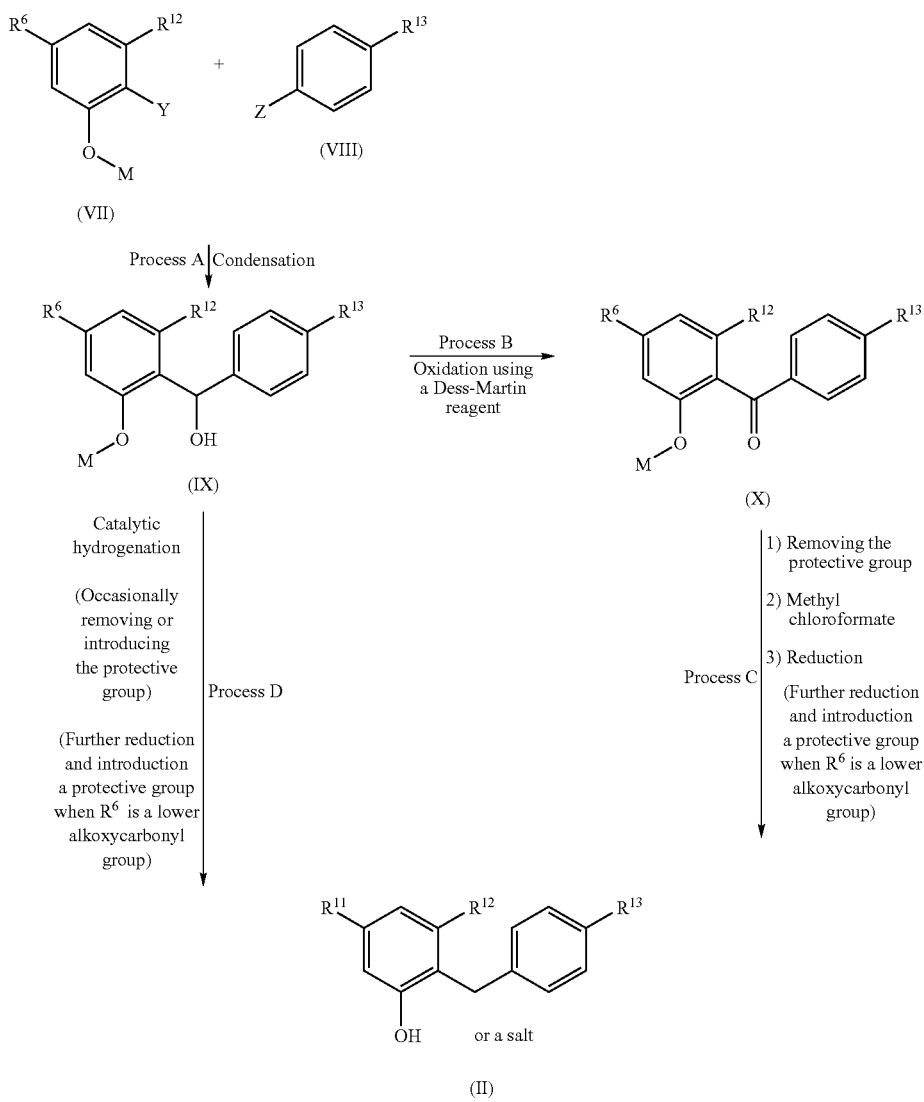

wherein M represents hydrogen atom or a hydroxy-protective group; $R^6$ represents a hydrogen atom, a protected hydroxy group, a protected amino group, a protected mono(lower alkyl)amino group, a di(lower alkyl)amino group, a carbamoyl group, a lower alkyl group, a lower alkoxy group, a protected hydroxy(lower alkyl) group, a protected hydroxy(lower alkoxy) group, a lower alkoxy-substituted (lower alkyl) group, a lower alkoxy-substituted (lower alkoxy) group, a carbamoyl (lower alkyl) group, a lower alkoxycarbonyl-substituted (lower alkyl) group, a lower alkoxycarbonyl-substituted (lower alkoxy) group, a carboxy-(lower alkyl) group, a carboxy(lower alkoxy) group or a lower alkoxycarbonyl group; one of Y and Z represents MgBr, MgCl, MgI or a lithium atom, while the other represents a formyl group; and $R^{11}$, $R^{12}$ and $R^{13}$ have the same meanings as defined above.

Process A

A compound represented by the above general formula (IX) can be prepared by condensing a benzaldehyde derivative represented by the above general formula (VII) with a Grignard reagent or a lithium reagent represented by the above general formula (VIII), or by condensing a Grignard reagent or a lithium reagent represented by the above general formula (VII) with a benzaldehyde derivative represented by the above general formula (VIII) in an inert solvent. As the solvent used, tetrahydrofuran, diethyl ether, a mixed solvent thereof and the like can be illustrated. The reaction temperature is usually from −78° C. to reflux temperature, and the reaction time is usually from 10 minutes to 1 day, varying based on a used starting material, solvent and reaction temperature.

Process B

A compound represented by the above general formula (X) can be prepared by subjecting a compound represented by the above general formula (IX) to oxidation using a Dess-Martin reagent in an inert solvent. As the solvent used, dichloromethane, chloroform, acetonitrile, a mixed solvent thereof and the like can be illustrated. The reaction temperature is usually from 0° C. to reflux temperature, and the reaction time is usually from 1 hour to 1 day, varying based on a used starting material, solvent and reaction temperature.

Process C

A compound represented by the above general formula (II) of the present invention can be prepared by removing the protective group of a compound represented by the above general formula (X) in the usual way, condensing the resulting compound with methyl chloroformate in the presence of a base such as triethylamine, diisopropylethylamine or 4-(N,N-dimethyl-amino)pyridine in an inert solvent and subjecting the resulting carbonate compound to reduction using a reducing agent such as sodium borohydride. As the solvent used in the condensing reaction, tetrahydrofuran, dichloromethane, acetonitrile, ethyl acetate, diethyl ether, a mixed solvent thereof and the like can be illustrated. The reaction temperature is usually from 0° C. to reflux temperature, and the reaction time is usually from 30 minutes to 1 day, varying based on a used starting material, solvent and reaction temperature. As the solvent used in the reducing reaction, a mixed solvent with tetrahydrofuran and water, and the like can be illustrated. The reaction temperature is usually from 0° C. to reflux temperature, and the reaction time is usually from 1 hour to 1 day, varying based on a used starting material, solvent and reaction temperature. In case that $R^6$ represents a lower alkoxycarbonyl group, the corresponding compounds can be derived into the compound represented by the above general formula (II) of the present invention by reducing said group using a reducing agent such as lithium aluminium hydride in an inert solvent into a hydroxymethyl group and protecting the hydroxy group in the usual way. As the solvent used in the reducing reaction, diethyl ether, tetrahydrofuran, a mixed solvent thereof and the like can be illustrated. The reaction temperature is usually from 0° C. to reflux temperature, and the reaction time is usually from 10 minutes to 1 day, varying based on a used starting material, solvent and reaction temperature. In addition, the compounds represented by the above general formula (II) of the present invention can be converted into a salt thereof such as a sodium salt or a potassium salt in the usual way.

Process D

A compound represented by the above general formula (II) of the present invention can be prepared by subjecting a compound represented by the above general formula (IX) to catalytic hydrogenation using a palladium catalyst such as palladium-carbon in the presence or absence of an acid such as hydrochloric acid in an inert solvent, and removing or introducing the protective group in the usual way as occasion demands. As the solvent used in the catalytic hydrogenation, methanol, ethanol, tetrahydrofuran, ethyl acetate, acetic acid, isopropanol, a mixed solvent thereof and the like can be illustrated. The reaction temperature is usually from room temperature to reflux temperature, and the reaction time is usually from 30 minutes to 1 day, varying based on a used starting material, solvent and reaction temperature. In case that $R^6$ represents a lower alkoxycarbonyl group, the corresponding compounds can be derived into the compound represented by the above general formula (II) of the present invention by reducing said group using a reducing agent such as lithium aluminium hydride in an inert solvent into a hydroxymethyl group and protecting the hydroxy group in the usual way. As the solvent used in the reducing reaction, diethyl ether, tetrahydrofuran, a mixed solvent thereof and the like can be illustrated. The reaction temperature is usually from 0° C. to reflux temperature, and the reaction time is usually from 10 minutes to 1 day, varying based on a used starting material, solvent and reaction temperature. In addition, the compound of the above general formula (II) of the present invention can be converted into a salt thereof such as a sodium salt or a potassium salt in the usual way.

In the compounds represented by the above general formulae (II), (VII), (VIII), (IX) and (X), compounds wherein substituents $R^{11}$ and/or $R^{13}$ represent a carboxy group, an amino group, a cyano group, a carbamoyl group, a hydroxy(lower alkyl) group, a carboxy(lower alkyl) group, a carboxy(lower alkenyl) group, a lower alkoxycarbonyl-substituted (lower alkyl) group, a lower alkoxycarbonyl-substituted (lower alkenyl) group, an amino(lower alkyl) group, a cyano(lower alkyl) group, a carbamoyl(lower alkyl) group or the like can be prepared by converting appropriately from the corresponding compound having a lower alkoxycarbonyl group as a substituent in the usual way and can be used in the subsequent processes (processes A–D and 1).

The compounds represented by the above general formula (II) of the present invention which are used as starting materials in the aforementioned production process and salts thereof can be also prepared according the following procedure:

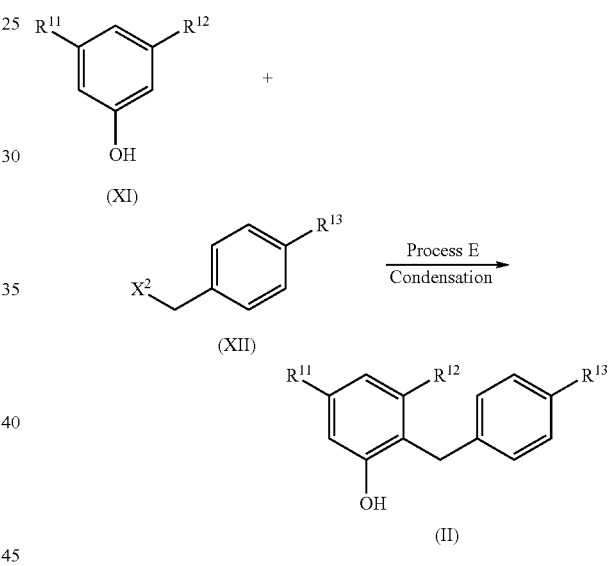

wherein $X^2$ represents a leaving group such as a chlorine atom; and $R^{11}$, $R^{12}$ and $R^{13}$ have the same meanings as defined above.

Process E

A compound represented by the above general formula (II) can be prepared by subjecting a phenol derivative represented by the above general formula (XI) to benzylation using a benzyl derivative represented by the above general formula (XII) in the presence of an alkaline material such as lithium hydroxide without any solvent. The reaction temperature is usually from 50 to 200° C., and the reaction time is usually from 30 minutes to 1 day, varying based on a used starting material, solvent and reaction temperature.

The compounds of the present invention obtained by the above production processes can be isolated and purified by conventional separation means such as fractional recrystallization, purification using chromatography, solvent extraction and solid phase extraction.

The glucopyranosyloxybenzylbenzene derivatives represented by the above general formula (I) of the present invention can be converted into their pharmaceutically acceptable salts in the usual way. Examples of the such salts include acid addition salts with mineral acids (e.g., hydrochloric acid, hydrobromic acid, sulfuric acid, nitric acid, phosphoric acid and the like), acid addition salts with organic acids (e.g., acetic acid, adipic acid, citric acid, fumaric acid, maleic acid, oleic acid, lactic acid, stearic acid, succinic acid, tartaric acid, methanesulfonic acid, benzenesulfonic acid, p-toluenesulfonic acid and the like), salts with organic amines (e.g., 2-aminoethanol, piperidine, morpholine, pyrrolidine and the like), and salts with inorganic base such as a sodium salt, a potassium salt, a calcium salt or a magnesium salt.

The compounds represented by the above general formula (I) of the present invention include their hydrates and their solvates with pharmaceutically acceptable solvents such as ethanol.

Of the compounds represented by the above general formula (I) of the present invention, compounds having an unsaturated bond exist in two geometrical isomer forms. Either cis(Z)-isomer or trans(E)-isomer can be employed in the present invention.

Of the compounds represented by the above general formula (I) of the present invention, compounds having an asymmetric carbon atom with the exception of the glucopyranosyloxy moiety exist in two optical isomer forms of (R) configuration and (S) configuration. Either one of the isomers or a mixture thereof can be employed in the present invention.

The compounds represented by the above general formula (I) and the pharmaceutically acceptable salts thereof of the present invention have an excellent inhibitory activity in human SGLT2 and are extremely useful as agents for the prevention or treatment of a disease associated with hyperglycemia such as diabetes, diabetic complication or obesity. In the following assay for inhibitory effect on human SGLT2 activity, compounds of the present invention exerted a potent inhibitory activity in human SGLT2.

When the pharmaceutical compositions of the present invention are employed in the practical treatment, various dosage forms are used depending on their uses. As examples of the dosage forms, powders, granules, fine granules, dry sirups, tablets, capsules, injections, solutions, ointments, suppositories, poultices and the like are illustrated, which are orally or parenterally administered.

These pharmaceutical compositions can be prepared by admixing with or by diluting and dissolving an appropriate pharmaceutical additive such as excipients, disintegrators, binders, lubricants, diluents, buffers, isotonicities, antiseptics, moistening agents, emulsifiers, dispersing agents, stabilizing agents, dissolving aids and the like, and formulating the mixture in accordance with conventional.

When the pharmaceutical compositions of the present invention are employed in the practical treatment, the dosage of a compound represented by the above general formula (I) or a pharmaceutically acceptable salt thereof of the present invention as the active ingredient is appropriately decided depending on the age, sex, body weight and degree of symptoms and treatment of each patient, which is approximately within the range of from 0.1 to 1,000 mg per day per adult human in the case of oral administration and approximately within the range of from 0.01 to 300 mg per day per adult human in the case of parenteral administration, and the daily dose can be divided into one to several doses per day and administered suitably.

EXAMPLE

The present invention is further illustrated in more detail by way of the following Reference Examples, Examples and Test Examples. However, the present invention is not limited thereto.

Reference Example 1

Methyl 4-[(2-benzyloxyphenyl)hydroxymethyl]benzoate

A Grignard reagent was prepared from 1-benzyloxy-2-bromobenzene (5.3 g), magnesium (0.49 g) and tetrahydrofuran (160 mL). The obtained Grignard reagent was added to a solution of methyl 4-formylbenzoate (3.3 g) in tetrahydrofuran (60 mL), and the mixture was stirred at room temperature for 1 hour. To the reaction mixture were added water and dilute hydrochloric acid, and the resulting mixture was extracted with ethyl acetate. The organic layer was washed with brine and dried over anhydrous sodium sulfate, and the solvent was removed under reduced pressure. The residue was purified by column chromatography on aminopropyl silica gel (eluent: hexane/ethyl acetate=4/1) to give methyl 4-[(2-benzyloxyphenyl)hydroxymethyl]benzoate (2.6 g).

$^1$H-NMR (CDCl$_3$) δ ppm: 3.02 (1H, d, J=6.3 Hz), 3.91 (3H, s), 5.00 (1H, d, J=11.6 Hz), 5.04 (1H, d, J=11.6 Hz), 6.07 (1H, d, J=6.3 Hz), 6.90–7.05 (2H, m), 7.15–7.35 (7H, m), 7.35–7.45 (2H, m), 7.90–8.00 (2H, m)

Example 1

Methyl 4-(2-hydroxybenzyl)benzoate

To a solution of methyl 4-[(2-benzyloxyphenyl)-hydroxymethyl]benzoate (2.6 g) in ethanol (15 mL) was added 10% palladium-carbon powder (0.50 g), and the mixture was stirred under a hydrogen atmosphere at room temperature for 18 hours. An insoluble material was removed by filtration, and the solvent of the filtrate was removed under reduced pressure to give methyl 4-(2-hydroxybenzyl)benzoate (1.7 g).

$^1$H-NMR (CDCl$_3$) δ ppm: 3.89 (3H, s), 4.04 (2H, s), 4.80 (1H, s), 6.75–6.80 (1H, m), 6.85–6.95 (1H, m), 7.05–7.20 (2H, m), 7.25–7.35 (2H, m), 7.90–8.00 (2H, m)

Reference Example 2

Methyl 4-(2-benzyloxybenzyl)benzoate

To a suspension of methyl 4-(2-hydroxybenzyl)benzoate (1.5 g) and potassium carbonate (0.94 g) in N,N-dimethylformamide (200 mL) was added benzylbromide (0.81 mL), and the mixture was stirred at 50° C. for 5 hours. An insoluble material was removed by filtration, water and dilute hydrochloric acid was added to the filtrate, and the mixture was extracted with ethyl acetate. The organic layer was washed with brine and dried over anhydrous magnesium sulfate, and the solvent was removed under reduced pressure. The residue was purified by column chromatography on silica gel (eluent: hexane/ethyl acetate=4/1) to give methyl 4-(2-benzyloxybenzyl)benzoate (2.1 g).

$^1$H-NMR (CDCl$_3$) δ ppm: 3.89 (3H, s), 4.06 (2H, s), 5.03 (2H, s), 6.85–6.95 (2H, m), 7.10–7.40 (9H, m), 7.85–7.95 (2H, m)

Reference Example 3

4-(2-Benzyloxybenzyl)benzyl alcohol

To a suspension of lithium aluminum hydride (0.47 g) in tetrahydrofuran (5 mL) was added dropwise a solution of methyl 4-(2-benzyloxybenzyl)benzoate (2.1 g) in tetrahydrofuran (5 mL) at 0° C., and the mixture was stirred at the same temperature for 1 hour. Ethyl acetate (10 mL) was added to the reaction mixture, and the resulting mixture was stirred for 30 minutes. To the reaction mixture were added water and dilute hydrochloric acid, and the mixture was extracted with ethyl acetate. The organic layer was washed with brine and dried over anhydrous magnesium sulfate, and the solvent was removed under reduced pressure to give 4-(2-benzyloxybenzyl)benzyl alcohol (1.9 g).

$^1$H-NMR (CDCl$_3$) δ ppm: 4.02 (2H, s), 4.65 (2H, s), 5.06 (2H, s), 6.85–6.95 (2H, m), 7.05–7.40 (11H, m)

Reference Example 4

4-(2-Benzyloxybenzyl)benzaldehyde

To a solution of 4-(2-benzyloxybenzyl)benzyl alcohol (1.0 g) in dichloromethane (50 mL) was added manganese (II) oxide (10 g), and the mixture was stirred at room temperature for 3 hours. An insoluble material was removed by filtration, and the solvent of the filtrate was removed under reduced pressure to give 4-(2-benzyloxybenzyl)benzaldehyde (0.97 g).

$^1$H-NMR (CDCl$_3$) δ ppm: 4.08 (2H, s), 5.03 (2H, s), 6.90–7.00 (2H, m), 7.10–7.40 (9H, m), 7.70–7.80 (2H, m), 9.96 (1H, s)

Reference Example 5

Ethyl (E)-3-[4-(2-hydroxybenzyl)phenyl]acrylate

To a solution of triethyl phosphonoacetate (0.89 mL) in tetrahydrofuran (30 mL) was added potassium tert-butoxide (0.50 g), and the mixture was stirred at room temperature for 15 minutes. A solution of 4-(2-benzyloxybenzyl)benzaldehyde (1.0 g) in tetrahydrofuran (10 mL) was added to the reaction mixture, and the mixture was stirred at room temperature for 6 hours. To the reaction mixture was added dilute hydrochloric acid, and the resulting mixture was extracted with ethyl acetate. The organic layer was washed with brine and dried over anhydrous magnesium sulfate, and the solvent was removed under reduced pressure. The residue was purified by column chromatography on silica gel (eluent: hexane/ethyl acetate=10/1) to give ethyl (E)-3-[4-(2-benzyloxybenzyl)phenyl]acrylate (0.86 g). To the obtained ethyl (E)-3-[4-(2-benzyloxybenzyl)phenyl]acrylate (0.86 g) were added trifluoroacetic acid (9.5 mL), water (0.5 mL) and dimethyl sulfide (1.0 mL), and the mixture was stirred at room temperature overnight. The solvent was removed under reduced pressure, and the residue was purified by column chromatography on silica gel (eluent: hexane/ethyl acetate=3/1) to give ethyl (E)-3-[4-(2-hydroxybenzyl)phenyl]acrylate (0.51 g).

$^1$H-NMR (CDCl$_3$) δ ppm: 1.33 (3H, t, J=7.2 Hz), 4.01 (2H, s), 4.26 (2H, q, J=7.2 Hz), 4.96 (1H, s), 6.38 (1H, d, J=16.1 Hz), 6.75–6.80 (1H, m), 6.85–6.95 (1H, m), 7.05–7.20 (2H, m), 7.20–7.30 (2H, m), 7.40–7.50 (2H, m), 7.65 (1H, d, J=16.1 Hz)

Reference Example 6

(E)-2-[4-(2-Ethoxycarbonylvinyl)benzyl]phenyl β-D-glucopyranoside

To a suspension of ethyl (E)-3-[4-(2-hydroxybenzyl)-phenyl]acrylate (0.34 g) and 1,2,3,4,6-penta-O-acetyl-β-D-glucopyranose (1.4 g) in dichloromethane (3 mL) and toluene (9 ml) was added boron trifluoride-diethyl ether complex (0.45 mL), and the mixture was stirred at room temperature overnight. The reaction mixture was concentrated under reduced pressure, and the residue was purified by column chromatography on silica gel (eluent: hexane/ethylacetate=4/1) to give (E)-2-[4-(2-ethoxy-carbonylvinyl)benzyl]phenyl 2,3,4,6-tetra-O-acetyl-β-D-glucopyranoside (0.47 g). To a solution of the obtained (E)-2-[(4-(2-ethoxycarbonylvinyl)benzyl]phenyl 2,3,4,6-tetra-O-acetyl-β-D-glucopyranoside (0.46 g) in methanol (5 mL) was added sodium methoxide (0.010 g), and the mixture was stirred at room temperature for 30 minutes. The reaction mixture was concentrated under reduced pressure, and the residue was purified by column chromatography on silica gel (eluent: ethyl acetate) to give (E)-2-[4-(2-ethoxycarbonylvinyl)benzyl]phenyl β-D-glucopyranoside (0.31 g).

$^1$H-NMR (CD$_3$OD) δ ppm: 1.31 (3H, t, J=7.2 Hz), 3.30–3.55 (4H, m), 3.68 (1H, dd, J=5.3, 12.0 Hz), 3.88 (1H, dd, J=1.9, 12.0 Hz), 4.00 (1H, d, J=14.9 Hz), 4.15 (1H, dd, J=14.9 Hz), 4.22 (2H, q, J=7.2 Hz), 4.92 (1H, d, J=7.1 Hz), 6.45 (1H, d, J=16.1 Hz), 6.90–7.00 (1H, m), 7.05–7.20 (3H, m), 7.25–7.35 (2H, m), 7.45–7.55 (2H, m), 7.64 (1H, d, J=16.1 Hz)

Reference Example 7

2-(4-Methoxycarbonylbenzyl)phenyl 2,3,4,6-tetra-O-acetyl-β-D-glucopyranoside To a suspension of methyl 4-(2-hydroxybenzyl)benzoate (0.053 g) and 1,2,3,4,6-penta-O-acetyl-β-D-glucopyranose (0.26 g) in dichloromethane (1 mL) and toluene (3 mL) was added boron trifluoride-diethyl ether complex (0.083 mL), and the mixture was stirred at room temperature overnight. The reaction mixture was concentrated under reduced pressure, and the residue was purified by column chromatography on silica gel (eluent: hexane/ethyl acetate=4/1) to give 2-(4-methoxycarbonyl-benzyl)phenyl 2,3,4,6-tetra-O-acetyl-β-D-glucopyranoside (0.067 g).

$^1$H-NMR (CDCl$_3$) δ ppm: 1.87 (3H, s), 2.03 (3H, s), 2.05 (3H, s), 2.07 (3H, s), 3.80–4.05 (6H, m), 4.16 (1H, dd, J=2.7, 12.4 Hz), 4.28 (1H, dd, J=5.8, 12.4 Hz), 5.10–5.20 (2H, m), 5.25–5.35 (2H, m), 6.95–7.10 (3H, m), 7.15–7.25 (3H, m), 7.90–7.95 (2H, m)

Reference Example 8

4-Allyloxy-2'-(methoxymethyloxy)diphenylmethanol

A Grignard reagent was prepared from 1-allyloxy-4-bromobenzene (1.7 g), magnesium (0.19 g), a catalytic amount of iodine and tetrahydrofuran (3 mL). To the obtained Grignard reagent was added a solution of 2-(methoxymethyloxy)-benzaldehyde (0.88 g) in tetrahydrofuran (19 mL), and the mixture was stirred at room temperature for 30 minutes. A saturated aqueous ammonium chloride solution was added to the reaction mixture, and the resulting mixture was extracted with ethyl acetate. The organic layer was washed with water and brine and dried over anhydrous sodium sulfate, and the solvent was removed under reduced pressure. The residue was purified by column chromatography on silica gel (eluent: hexane/ethyl acetate=5/1) to give 4-allyloxy-2'-(methoxymethyloxy)diphenylmethanol (1.2 g).

$^1$H-NMR (CDCl$_3$) δ ppm: 2.78 (1H, d, J=5.4 Hz), 3.31 (3H, s), 4.45–4.55 (2H, m), 5.12 (1H, d, J=7.0 Hz), 5.14 (1H, d, J=7.0 Hz), 5.20–5.30 (1H, m), 5.35–5.45 (1H, m), 5.95–6.10 (2H, m), 6.80–6.90 (2H, m), 6.95–7.05 (1H, m), 7.07 (1H, dd, J=0.9, 8.2 Hz), 7.20–7.35 (3H, m), 7.35 (1H, dd, J=1.8, 7.7 Hz)

Reference Example 9

4-Allyloxy-2'-(methoxymethyloxy)benzophenone

To a solution of 4-allyloxy-2'-(methoxymethyloxy)-diphenylmethanol (1.2 g) in dichloromethane (20 mL) was added a Dess-Martin reagent (1,1,1-tris(acetyloxy)-1,1-dihydro-1,2-benziodoxol-3-(1H)-one) (2.1 g) at 0° C., and the mixture was stirred for 1 hour. The reaction mixture was warmed to ambient temperature and stirred overnight. Diethyl ether and 1 mol/L aqueous sodium hydroxide solution were added to the reaction mixture, and the organic layer was separated. The organic layer was washed with 1 mol/L aqueous sodium hydroxide solution, water and brine, and dried over anhydrous magnesium sulfate, and the solvent was removed under reduced pressure to give 4-allyloxy-2'-(methoxymethyloxy)benzophenone (1.1 g).

$^1$H-NMR (CDCl$_3$) δ ppm: 3.33 (3H, s), 4.55–4.65 (2H, m), 5.08 (2H, s), 5.25–5.35 (1H, m), 5.35–5.50 (1H, m), 6.00–6.15 (1H, m), 6.85–7.00 (2H, m), 7.05–7.15 (1H, m), 7.15–7.25 (1H, m), 7.33 (1H, dd, J=1.5, 7.7 Hz), 7.35–7.50 (1H, m), 7.75–7.85 (2H, m)

Reference Example 10

4-Allyloxy-2'-hydroxybenzophenone

To a solution of 4-allyloxy-2'-(methoxymethyloxy)-benzophenone (1.1 g) in ethanol (15 mL) was added concentrated hydrochloric acid (0.96 mL), and the mixture was stirred at room temperature overnight. The reaction mixture was concentrated under reduced pressure, and a saturated aqueous sodium hydrogen carbonate solution was added to the residue. The mixture was extracted with ethyl acetate. The organic layer was washed with brine and dried over anhydrous sodium sulfate, and the solvent was removed under reduced pressure. The residue was purified by column chromatography on silica gel (eluent: hexane/ethyl acetate=15/1) to give 4-allyloxy-2'-hydroxybenzophenone (0.87 g).

$^1$H-NMR (CDCl$_3$) δ ppm: 4.60–4.70 (2H, m), 5.30–5.40 (1H, m), 5.40–5.50 (1H, m), 6.00–6.15 (1H, m), 6.85–6.95 (1H, m), 6.95–7.05 (2H, m), 7.07 (1H, dd, J=1.0, 8.4 Hz), 7.45–7.55 (1H, m), 7.63 (1H, dd, J=1.6, 8.0 Hz), 7.65–7.75 (2H, m), 11.96 (1H, s)

Example 2

2-(4-Allyloxybenzyl)phenol

To a solution of 4-allyloxy-2'-hydroxybenzophenone (0.87 g) in tetrahydrofuran (14 mL) were added triethylamine (0.53 mL) and methyl chloroformate (0.29 mL) at 0° C., and the mixture was stirred at room temperature for 1.5 hours. An insoluble material was removed by filtration, and the solvent of the filtrate was removed under reduced pressure. To a solution of the residue in tetrahydrofuran (18 mL) and water (9 mL) was added sodium borohydride (0.52 g) at 0° C., and the mixture was stirred at room temperature for 2.5 hours. To the reaction mixture was added 0.5 mol/L aqueous hydrochloric acid solution, and the mixture was extracted with ethyl acetate. The organic layer was washed with water and brine, and dried over anhydrous sodium sulfate, and the solvent was removed under reduced pressure. The residue was purified by column chromatography on silica gel (eluent: hexane/ethyl acetate=8/1) to give 2-(4-allyloxybenzyl)phenol (0.72 g).

$^1$H-NMR (CDCl$_3$) δ ppm: 3.93 (2H, s), 4.45–4.55 (2H, m), 4.73 (1H, brs), 5.20–5.30 (1H, m), 5.35–5.45 (1H, m), 5.95–6.10 (1H, m), 6.78 (1H, dd, J=1.3, 7.9 Hz), 6.80–6.95 (3H, m), 7.05–7.20 (4H, m)

Reference Example 11

2-(4-Allyloxybenzyl)phenyl 2,3,4,6-tetra-O-acetyl-β-D-glucopyranoside

To a solution of 2-(4-allyloxybenzyl)phenol (0.20 g) and 2,3,4,6-tetra-O-acetyl-1-O-trichloroacetoimidoyl-α-D-glucopyranose (0.45 g) in dichloromethane (8.5 mL) was added boron trifluoride-diethyl ether complex (0.12 g), and the mixture was stirred at room temperature for 2 hours. A saturated aqueous sodium hydrogen carbonate solution was added to the reaction mixture, and the resulting mixture was extracted with ethyl acetate. The organic layer was washed with brine and dried over anhydrous sodium sulfate, and the solvent was removed under reduced pressure. The residue was purified by column chromatography on silica gel (eluent: hexane/ethyl acetate=1/1) to give 2-(4-allyloxybenzyl)phenyl 2,3,4,6-tetra-O-acetyl-β-D-glucopyranoside (0.44 g).

$^1$H-NMR (CDCl$_3$) δ ppm: 1.90 (3H, s), 2.03 (3H, s), 2.05 (3H, s), 2.07 (3H, s), 3.80–3.95 (3H, m), 4.18 (1H, dd, J=2.5, 12.3 Hz), 4.28 (1H, dd, J=5.5, 12.3 Hz), 4.45–4.55 (2H, m), 5.11 (1H, d, J=7.5 Hz), 5.10–5.45 (5H, m), 5.95–6.10 (1H, m), 6.75–6.85 (2H, m), 6.95–7.10 (5H, m), 7.10–7.20 (1H, m)

Reference Example 12

4-(2-Benzyloxyethyl)-2'-(methoxymethyloxy)diphenylmethanol

The title compound was prepared in a similar manner to that described in Reference Example 8 using 4-(2-benzyloxy-ethyl)-1-bromobenzene instead of 4-allyloxy-1-bromobenzene.

$^1$H-NMR (CDCl$_3$) δ ppm: 2.80 (1H, d, J=5.7 Hz), 2.90 (2H, t, J=7.1 Hz), 3.30 (3H, s), 3.66 (2H, t, J=7.1 Hz), 4.51 (2H, s), 5.10–5.20 (2H, m), 6.06 (1H, d, J=5.7 Hz), 6.95–7.05 (1H, m), 7.05–7.10 (1H, m), 7.10–7.20 (2H, m), 7.20–7.40 (9H, m)

Reference Example 13

4-(2-Benzyloxyethyl)-2'-(methoxymethyloxy)benzophenone

The title compound was prepared in a similar manner to that described in Reference Example 9 using 4-(2-benzyloxyethyl)-2'-(methoxymethyloxy)diphenylmethanol instead of 4-allyloxy-2'-(methoxymethyloxy)diphenylmethanol.

¹H-NMR (CDCl₃) δ ppm: 2.98 (2H, t, J=6.8 Hz), 3.29 (3H, s), 3.72 (2H, t, J=6.8 Hz), 4.51 (2H, s), 5.05 (2H, s), 7.05–7.15 (1H, m), 7.15–7.25 (1H, m), 7.25–7.40 (8H, m), 7.40–7.50 (1H, m), 7.70–7.80 (2H, m)

Reference Example 14

4-(2-Benzyloxyethyl)-2'-hydroxybenzophenone

The title compound was prepared in a similar manner to that described in Reference Example 10 using 4-(2-benzyloxyethyl)-2'-(methoxymethyloxy)benzophenone instead of 4-allyloxy-2'-(methoxymethyloxy)benzophenone.

¹H-NMR (CDCl₃) δ ppm: 3.02 (2H, t, J=6.8 Hz), 3.75 (2H, t, J=6.8 Hz), 4.55 (2H, s), 6.85–6.90 (1H, m), 7.05–7.10 (1H, m), 7.25–7.40 (7H, m), 7.45–7.55 (1H, m), 7.55–7.65 (3H, m), 12.02 (1H, s)

Example 3

2-[4-(2-Benzyloxyethyl)benzyl]phenol

The title compound was prepared in a similar manner to that described in Example 2 using 4-(2-benzyloxyethyl)-2'-hydroxybenzophenone instead of 4-allyloxy-2'-hydroxybenzophenone.

¹H-NMR (CDCl₃) δ ppm: 2.90 (2H, t, J=7.2 Hz), 3.66 (2H, t, J=7.2 Hz), 3.97 (2H, s), 4.52 (2H, s), 4.62 (1H, s), 6.75–6.85 (1H, m), 6.85–6.95 (1H, m), 7.05–7.20 (6H, m), 7.20–7.40 (5H, m)

Reference Example 15

4-(2-Benzyloxybenzyl)benzyl chloride

To a solution of 4-(2-benzyloxybenzyl)benzyl alcohol (0.67 g) in dichloromethane (30 mL) was added thionyl chloride (0.48 mL), and the mixture was heated under reflux for 1 hour. The reaction mixture was concentrated under reduced pressure, water was added to the residue, and the resulting mixture was extracted with diethyl ether. The organic layer was washed with brine and dried over anhydrous sodium sulfate, and the solvent was removed under reduced pressure to give 4-(2-benzyloxy-benzyl) benzyl chloride (0.68 g).

¹H-NMR (CDCl₃) δ ppm: 4.01 (2H, s), 4.56 (2H, s), 5.04 (2H, s), 6.85–7.40 (13H, m)

Reference Example 16

[4-(2-Benzyloxybenzyl)phenyl]acetonitrile

To a solution of 4-(2-benzyloxybenzyl)benzyl chloride (0.66 g) in N,N-dimethylformamide (20 mL) was added potassium cyanide (0.40 g), and the mixture was stirred at 60° C. for 18 hours. The reaction mixture was cooled to ambient temperature, and water was added thereto. The resulting mixture was extracted with ethyl acetate. The organic layer was washed with a saturated aqueous sodium hydrogen carbonate solution and brine, and dried over anhydrous magnesium sulfate, and the solvent was removed under reduced pressure. The residue was purified by column chromatography on silica gel (eluent: hexane/ethyl acetate=5/1–3/1) to give [4-(2-benzyloxybenzyl)phenyl]acetonitrile (0.54 g).

¹H-NMR (CDCl₃) δ ppm: 3.70 (2H, s), 4.01 (2H, s), 5.04 (2H, s), 6.85–7.40 (13H, m)

Example 4

[4-(2-Hydroxybenzyl)phenyl]acetonitrile

Trifluoroacetic acid (17 mL), water (1 mL) and dimethyl sulfide (2 mL) were added to [4-(2-benzyloxybenzyl)phenyl]-acetonitrile (0.41 g), and the mixture was stirred at room temperature overnight. The reaction mixture was concentrated under reduced pressure, and the residue was purified by column chromatography on silica gel (eluent: hexane/ethyl acetate=3/1) to give [4-(2-hydroxybenzyl)phenyl]acetonitrile (0.26 g).

¹H-NMR (CDCl₃) δ ppm: 3.71 (2H, s), 3.99 (2H, s), 4.76 (1H, s), 6.77 (1H, dd, J=1.1, 7.9 Hz), 6.89 (1H, dt, 1.1, 7.5 Hz), 7.05–7.20 (2H, m), 7.20–7.30 (4H, m)

Reference Example 17

4-(2-Benzyloxybenzyl)benzoic acid

To a solution of methyl 4-(2-benzyloxybenzyl)benzoate (1.0 g) in methanol (20 mL) was added 2 mol/L aqueous sodium hydroxide solution (7.5 mL), and the mixture was stirred at 60° C. for 5 hours. The reaction mixture was concentrated under reduced pressure. After the residue was acidified by adding dilute hydrochloric acid, the resulting mixture was extracted with ethyl acetate. The organic layer was washed with brine, and dried over anhydrous magnesium sulfate, and the solvent was removed under reduced pressure to give 4-(2-benzyloxybenzyl)benzoic acid (0.72 g).

¹H-NMR (DMSO-d₆) δ ppm: 4.01 (2H, s), 5.09 (2H, s), 6.85–6.95 (1H, m), 7.00–7.10 (1H, m), 7.15–7.40 (9H, m), 7.75–7.85 (2H, m), 12.77 (1H, brs)

Reference Example 18

4-(2-Benzyloxybenzyl)benzamide

To a suspension of 4-(2-benzyloxybenzyl)benzoic acid (0.70 g) in dichloromethane (10 mL) was added thionyl chloride (0.48 mL), and the mixture was stirred at 50° C. for 3 hours. The reaction mixture was concentrated under reduced pressure, and 28% aqueous ammonium solution (50 mL) was added to the residue. The mixture was stirred at room temperature for 30 minutes. An insoluble material was collected by filtration, washed with water then hexane, and dried under reduced pressure to give 4-(2-benzyloxybenzyl)benzamide (0.62 g).

¹H-NMR (DMSO-d₆) δ ppm: 3.98 (2H, s), 5.10 (2H, s), 6.85–6.95 (1H, m), 7.00–7.10 (1H, m), 7.15–7.40 (10H, m), 7.70–7.80 (2H, m), 7.88 (1H, brs)

Example 5

4-(2-Hydroxybenzyl)benzamide

To a solution of 4-(2-benzyloxybenzyl)benzamide (0.50 g) in ethanol (10 mL) was added 10% palladium-carbon powder (0.10 μg), and the mixture was stirred under a hydrogen atmosphere at room temperature for 1 hour. An insoluble material was removed by filtration, and the solvent of the filtrate was removed under reduced pressure to give 4-(2-hydroxybenzyl)benzamide (0.31 g).

¹H-NMR (DMSO-d₆) δ ppm: 3.90 (2H, s), 6.65–6.75 (1H, m), 6.75–6.85 (1H, m), 6.95–7.10 (2H, m), 7.20–7.30 (3H, m), 7.70–7.80 (2H, m), 7.86 (1H, brs), 9.40 (1H, s)

Reference Example 19

2-Benzyloxy-4'-(N,N-dimethylamino)diphenyl-methanol

The title compound was prepared in a similar manner to that described in Reference Example 8 using 2-benzyloxy-1-bromobenzene and 4-(N,N-dimethylamino)benzaldehyde instead of 4-allyloxy-1-bromobenzene and 2-(methoxymethyloxy)-benzaldehyde.

$^1$H-NMR (CDCl$_3$) δ ppm: 2.77 (1H, d, J=5.3 Hz), 2.93 (6H, s), 5.04 (2H, s), 6.03 (1H, d, J=5.3 Hz), 6.65–6.75 (2H, m), 6.85–7.05 (2H, m), 7.15–7.45 (9H, m)

Example 6

2-[4-(N,N-Dimethylamino)benzyl]phenol

To a solution of 2-benzyloxy-4'-(N,N-dimethylamino)-diphenylmethanol (0.85 g) in ethanol (25 mL) was added 10% palladium-carbon powder (0.34 g), and the mixture was stirred under a hydrogen atmosphere at room temperature for 22 hours. An insoluble material was removed by filtration, and the solvent of the filtrate was removed under reduced pressure. The residue was purified by column chromatography on silica gel (eluent: hexane/ethyl acetate=4/1) to give 2-[4-(N,N-dimethylamino)-benzyl]phenol (0.35 g).

$^1$H-NMR (CDCl$_3$) δ ppm: 2.91 (6H, s), 3.91 (2H, s), 4.73 (1H, s), 6.65–6.75 (2H, m), 6.75–6.85 (1H, m), 6.85–6.95 (1H, m), 7.05–7.20 (4H, m)

Reference Example 20

2-[4-(N,N-Dimethylamino)benzyl]phenyl 2,3,4,6-tetra-O-acetyl-β-D-glucopyranoside The title compound was prepared in a similar manner to that described in Reference Example 11 using 2-[4-(N,N-dimethyl-amino)benzyl]phenol instead of 2-(4-allyloxybenzyl)phenol.

$^1$H-NMR (CDCl$_3$) δ ppm: 1.92 (3H, s), 2.03 (3H, s), 2.05 (3H, s), 2.08 (3H, s), 2.89 (6H, s), 3.80–3.90 (3H, m), 4.18 (1H, dd, J=2.3, 12.2 Hz), 4.28 (1H, dd, J=5.7, 12.2 Hz), 5.09 (1H, d, J=7.7 Hz), 5.15–5.25 (1H, m), 5.25–5.40 (2H, m), 6.60–6.70 (2H, m), 6.90–7.10 (5H, m), 7.10–7.20 (1H, m)

Reference Example 21

4-Benzyloxy-2'-(methoxymethyloxy)diphenylmethanol

The title compound was prepared in a similar manner to that described in Reference Example 8 using 1-bromo-2-(methoxy-methyloxy)benzene and 4-benzyloxybenzaldehyde instead of 1-allyloxy-4-bromobenzene and 2-(methoxymethyloxy)-benzaldehyde.

$^1$H-NMR (CDCl$_3$) δ ppm: 2.78 (1H, d, J=5.4 Hz), 3.29 (3H, s), 5.04 (2H, s), 5.10–5.20 (2H, m), 6.03 (1H, d, J=5.4 Hz), 6.85–6.95 (2H, m), 6.95–7.10 (2H, m), 7.20–7.45 (9H, m)

Reference Example 22

4-Benzyoxy-2'-(methoxymethyloxy)benzophenone

The title compound was prepared in a similar manner to that described in Reference Example 9 using 4-benzyloxy-2'-(methoxymethyloxy)diphenylmethanol instead of 4-allyloxy-2'-(methoxymethyloxy)diphenylmethanol.

$^1$H-NMR (CDCl$_3$) δ ppm: 3.31 (3H, s), 5.07 (2H, s), 5.13 (2H, s), 6.95–7.05 (2H, m), 7.05–7.15 (1H, m), 7.15–7.25 (1H, m), 7.30–7.50 (7H, m), 7.75–7.85 (2H, m)

Reference Example 23

4-Benxyloxy-2'-hydroxybenzophenone

The title compound was prepared in a similar manner to that described in Reference Example 10 using 4-benzyloxy-2'-(methoxymethyloxy)benzophenone instead of 4-allyloxy-2'-(methoxymethyloxy)benzophenone.

$^1$H-NMR (CDCl$_3$) δ ppm: 5.16 (2H, s), 6.85–6.95 (1H, m), 7.00–7.10 (3H, m), 7.30–7.55 (6H, m), 7.63 (1H, dd, J=1.9, 8.2 Hz), 7.65–7.75 (2H, m), 11.95 (1H, s)

Example 7

2-[(4-Benzyloxy)benzyl]phenol

The title compound was prepared in a similar manner to that described in Example 2 using 4-benzyloxy-2'-hydroxybenzophenone instead of 4-allyloxy-2'-hydroxybenzophenone.

$^1$H-NMR (CDCl$_3$) δ ppm: 3.94 (2H, s), 4.70 (1H, s), 5.03 (2H, s), 6.75–6.80 (1H, m), 6.85–6.95 (3H, m), 7.05–7.20 (4H, m), 7.25–7.45 (5H, m)

Reference Example 24

2-[(4-Benzyloxy)benzyl]phenyl 2,3,4,6-tetra-O-acetyl-β-D-glucopyranoside

The title compound was prepared in a similar manner to that described in Reference Example 11 using 2-[4-(benzyloxy)-benzyl]phenol instead of 2-(4-allyloxybenzyl)phenol.

$^1$H-NMR (CDCl$_3$) δ ppm: 1.88 (3H, s), 2.03 (3H, s), 2.05 (3H, s), 2.07 (3H, s), 3.80–3.90 (3H, m), 4.17 (1H, dd, J=2.4, 12.3 Hz), 4.28 (1H, dd, J=5.7, 12.3 Hz), 5.03 (2H, s), 5.10 (1H, d, J=7.2 Hz), 5.15–5.25 (1H, m), 5.25–5.40 (2H, m), 6.85–6.90 (2H, m), 6.95–7.10 (5H, m), 7.10–7.20 (1H, m), 7.25–7.45 (5H, m)

Reference Example 25

1-Bromo-4-[2-(methoxymethyloxy)ethyl]benzene

To a solution of 2-(4-bromophenyl)ethanol (1.0 g) and diisopropylethylamine (1.3 mL) in dichloromethane (5 mL) was added chloromethyl methyl ether (0.75 mL), and the mixture was stirred at room temperature for 2 hours. To the reaction mixture was added water, and the organic layer was separated and dried over anhydrous sodium sulfate. The solvent was removed under reduced pressure. The residue was purified by column chromatography on silica gel (eluent: hexane/ethyl acetate=15/1–10/1) to give 1-bromo-4-[2-(methoxymethyloxy)ethyl]-benzene (1.2 g).

$^1$H-NMR (CDCl$_3$) δ ppm: 2.85 (2H, t, J=6.8 Hz), 3.28 (3H, s), 3.74 (2H, t, J=6.8 Hz), 4.60 (2H, s), 7.05–7.15 (2H, m), 7.35–7.45 (2H, m)

Reference Example 26

2-Hydroxy-4-methoxy-4'-[2-(methoxymethyloxy)ethyl]diphenyl-methanol

To a solution of 1-bromo-4-[2-(methoxymethyloxy)-ethyl]benzene (0.61 g) in tetrahydrofuran (12 mL) was added tert-butyl lithium (1.5 mol/L pentane solution, 1.8 mL) under an argon atmosphere at −78° C., and the mixture was stirred for 30 minutes. A solution of 2-hydroxy-4-methoxybenzaldehyde (0.15 g) in tetrahydrofuran (6 mL) was added to the reaction mixture, and the mixture was warmed to 0° C. and stirred for 25 minutes. A saturated aqueous ammonium chloride solution was added to the reaction mixture, and the mixture was extracted with diethyl ether. The organic layer was dried over anhydrous sodium sulfate, and the solvent was removed under reduced pressure. The residue was purified by column chromatography on silica gel (eluent: hexane/ethyl acetate=2/1) to give 2-hydroxy-4-methoxy-4'-[2-(methoxymethyloxy)ethyl]diphenyl-methanol (0.31 g).

$^1$H-NMR (CDCl$_3$) δ ppm: 2.77 (1H, d, J=2.9 Hz), 2.90 (2H, t, J=6.9 Hz), 3.29 (3H, s), 3.70–3.80 (5H, m), 4.61 (2H, s), 5.96 (1H, d, J=2.9 Hz), 6.35 (1H, dd, J=2.1, 8.5 Hz), 6.48 (1H, d, J=2.1 Hz), 6.70 (1H, d, J=8.5 Hz), 7.20–7.35 (4H, m), 8.04 (1H, s)

Example 8

5-Methoxy-2-{4-[2-(methoxymethyloxy)ethyl]benzyl}phenol

To a solution of 2-hydroxy-4-methoxy-4'-[2-(methoxymethyloxy)ethyl]diphenylmethanol(0.31 g) in ethanol(10 mL) was added 10% palladium-carbon powder (0.061 g), and the mixture was stirred under a hydrogen atmosphere at room temperature for 1 hour. An insoluble material was removed by filtration, and the solvent of the filtrate was removed under reduced pressure. The residue was purified by column chromatography on silica gel (eluent: hexane/ethyl acetate=5/2) to give 5-methoxy-2-{4-[2-(methoxymethyloxy)ethyl]benzyl}phenol (0.19 g).

$^1$H-NMR (CDCl$_3$) δ ppm: 2.86 (2H, t, J=7.0 Hz), 3.29 (3H, s), 3.74 (2H, t, J=7.0 Hz), 3.76 (3H, s), 3.90 (2H, s), 4.61 (2H, s), 4.77 (1H, s), 6.38 (1H, d, J=2.5 Hz), 6.45 (1H, dd, J=2.5, 8.5 Hz), 7.01 (1H, d, J=8.5 Hz), 7.10–7.20 (4H, m)

Reference Example 27

5-Methoxy-2-{4-[2-(methoxymethyloxy)ethyl]benzyl}phenyl 2,3,4,6-tetra-O-acetyl-β-D-glucopyranoside To a solution of 5-methoxy-2-{4-[2-(methoxymethyloxy)ethyl]benzyl}phenol (0.19 g) and 2,3,4,6-tetra-O-acetyl-1-O-trichloroacetoimidoyl-α-D-glucopyranose (0.40 g) in dichloromethane (15 mL) was added boron trifluoride-diethyl ether complex (0.088 mL) at 0° C., and the mixture was stirred 20 minutes. A saturated aqueous sodium hydrogen carbonate solution was added to the reaction mixture, and the organic layer was separated. The organic layer was dried over anhydrous sodium sulfate, and the solvent was removed under reduced pressure. The residue was purified by column chromatography on silica gel (eluent: hexane/ethyl acetate=1/1) to give 5-methoxy-2-{4-[2-(methoxymethyloxy)ethyl]benzyl}phenyl 2,3,4,6-tetra-O-acetyl-β-D-glucopyranoside (0.33 g).

$^1$H-NMR (CDCl$_3$) δ ppm: 1.85 (3H, s), 2.02 (3H, s), 2.05 (3H, s), 2.10 (3H, s), 2.85 (2H, t, J=7.1 Hz), 3.30 (3H, s), 3.72 (2H, t, J=7.1 Hz), 3.77 (3H, s), 3.75–3.85 (2H, m), 3.80–3.95 (1H, m), 4.19 (1H, dd, J=2.4, 12.2 Hz), 4.25 (1H, dd, J=5.9, 12.2 Hz), 4.60 (2H, s), 5.07 (1H, d, J=7.7 Hz), 5.10–5.20 (1H, m), 5.25–5.35 (2H, m), 6.53 (1H, dd, J=2.5, 8.7 Hz), 6.65 (1H, d, J=2.5 Hz), 6.94 (1H, d, J=8.7 Hz), 7.00–7.20 (4H, m)

Reference Example 28

Methyl 3-benzyloxy-4-(4-ethylbenzyl)benzoate

To a solution methyl 4-(4-ethylbenzyl)-3-hydroxybenzoate (1.28 g) in N,N-dimethylformamide (14 mL) were added potassium carbonate (0.98 g) and benzyl bromide (0.62 mL), and the mixture was stirred at room temperature for 19 hours. The reaction mixture was poured into water, and the mixture was extracted twice with diethyl ether. The combined organic layer was washed with water and dried over anhydrous magnesium sulfate, and the solvent was removed under reduced pressure. The residue was purified by column chromatography on silica gel (eluent: hexane/ethyl acetate=5/1) to give methyl 3-benzyloxy-4-(4-ethylbenzyl)benzoate (1.6 g).

$^1$H-NMR (CDCl$_3$) δ ppm: 1.22 (3H, t, J=7.7 Hz), 2.61 (2H, q, J=7.7 Hz), 3.90 (3H, s), 4.02 (2H, s), 5.11 (2H, s), 7.00–7.20 (5H, m), 7.25–7.40 (5H, m), 7.55–7.65 (2H, m)

Reference Example 29

3-Benzyloxy-4-(4-ethylbenzyl)benzoic acid

Methyl 3-benzyloxy-4-(4-ethylbenzyl)benzoate (1.6 g) was dissolved in a mixed solvent of tetrahydrofuran (5 mL) and ethanol (5 mL). To the solution was added 2 mol/L aqueous sodium hydroxide solution (10 mL), and the mixture was stirred at 80° C. for 1 hour. The reaction mixture was cooled to ambient temperature, acidified with 2 mol/L hydrochloric acid, and the mixture was stirred under ice-cooling for 30 minutes. The resulting precipitated crystals were collected by filtration, washed with water and dried to give 3-benzyloxy-4-(4-ethylbenzyl)benzoic acid (1.4 g).

$^1$H-NMR (DMSO-d$_6$) δ ppm: 1.14 (3H, t, J=7.6 Hz), 2.55 (2H, q, J=7.6 Hz), 3.96 (2H, s), 5.18 (2H, s), 7.05–7.15 (4H, m), 7.20–7.40 (6H, m), 7.50 (1H, dd, J=1.5, 7.9 Hz), 7.55 (1H, d, J=1.5 Hz), 12.84 (1H, s)

Example 9

5-Amino-2-(4-ethylbenzyl)phenol

To a solution of 3-benzyloxy-4-(4-ethylbenzyl)benzoic acid (1.4 g) and triethylamine (1.3 mL) in 1,4-dioxane (10 mL) was added a solution of diphenylphosphoryl azide (1.3 g) in 1,4-dioxane (10 mL), and the mixture was stirred at 100° C. for 1 hour. Benzyl alcohol (1.6 mL) was added to the reaction mixture, and the mixture was stirred at the same temperature for 7 hours. The solvent of the reaction mixture was removed under reduced pressure, and the residue was purified by column chromatography on silica gel (eluent: hexane/ethyl acetate=4/1) to give benzyl N-[3-benzyloxy-4-(4-ethylbenzyl)phenyl]carbamate (1.4 g). To a solution of obtained benzyl N-[3-benzyloxy-4-(4-ethyl-benzyl)phenyl]carbamate (1.4 g) in methanol (15 mL) was added 10% palladium-carbon powder (0.28 g), and the mixture was stirred under a hydrogen atmosphere for 11 hours. An insoluble material was removed by filtration, and the solvent of the filtrate was removed under reduced pressure. The residue was purified by column chromatography on silica gel (eluent: hexane/ethyl acetate=1/1) to give 5-amino-2-(4-ethylbenzyl)phenol(0.54 g).

$^1$H-NMR (CDCl$_3$) δ ppm: 1.21 (3H, t, J=7.7 Hz), 2.61 (2H, q, J=7.7 Hz), 3.56 (2H, brs), 3.85 (2H, s), 4.57 (1H, s), 6.18 (1H, d, J=2.4 Hz), 6.25 (1H, dd, J=2.4, 8.1 Hz), 6.89 (1H, d, J=8.1 Hz), 7.05–7.15 (4H, m)

Example 10

Benzyl N-[4-(4-ethylbenzyl)-3-hydroxyphenyl]carbamate

To a solution of 5-amino-2-(4-ethylbenzyl)phenol (0.25 g) in tetrahydrofuran (10 mL) was added N-benzyloxycarbonyloxy-succinimide (0.41 g), and the mixture was stirred at room temperature for 22 hours. The reaction mixture was purified by column chromatography on silica gel (eluent: hexane/ethyl acetate=5/1) to give benzyl N-[4-(4-ethylbenzyl)-3-hydroxyphenyl]carbamate (0.40 g).

$^1$H-NMR (CDCl$_3$) δ ppm: 1.21 (3H, t, J=7.7 Hz), 2.60 (2H, q, J=7.7 Hz), 3.90 (2H, s), 5.00 (1H, brs), 5.19 (2H, s), 6.59 (1H, brs), 6.70 (1H, dd, J=2.3, 8.2 Hz), 7.01 (1H, d, J=8.2 Hz), 7.05–7.20 (5H, m), 7.30–7.45 (5H, m)

Reference Example 30

5-Benzyloxycarbonylamino-2-(4-ethylbenzyl)phenyl 2,3,4,6-tetra-O-acetyl-β-D-glucopyranoside The title compound was prepared in a similar manner to that described in Reference Example 27 using benzyl N-[4-(4-ethylbenzyl)-3-hydroxyphenyl]carbamate instead of 5-methoxy-2-[4-(2-methoxymethyloxy)ethylbenzyl]phenol.

$^1$H-NMR (CDCl$_3$) δ ppm: 1.19 (3H, t, J=7.5 Hz), 1.85 (3H, s), 2.02 (3H, s), 2.03 (3H, s), 2.05 (3H, s), 2.59 (2H, q, J=7.5 Hz), 3.70–3.95 (3H, m), 4.10–4.40 (2H, m), 5.00–5.40 (6H, m), 6.63 (1H, brs), 6.74 (1H, dd, J=1.9, 8.2 Hz), 6.95 (1H, d, J=8.2 Hz), 6.95–7.10 (4H, m), 7.20–7.60 (6H, m)

Reference Example 31

5-Amino-2-(4-ethylbenzyl)phenyl 2,3,4,6-tetra-O-acetyl-β-D-glucopyranoside

To a solution of 5-benzyloxycarbonylamino-2-(4-ethylbenzyl)phenyl 2,3,4,6-tetra-O-acetyl-β-D-glucopyranoside (0.35 g) in tetrahydrofuran (4 mL) was added 10% palladium-carbon powder (0.07 g), and the mixture was stirred under a hydrogen atmosphere at room temperature for 8 hours. An insoluble material was removed by filtration, and the solvent of the filtrate was removed under reduced pressure. The residue was purified by column chromatography on silica gel (eluent: hexane/ethyl acetate=2/3-dichloromethane/ethyl acetate=1/1) to give 5-amino-2-(4-ethylbenzyl)phenyl 2,3,4,6-tetra-O-acetyl-β-D-glucopyranoside (0.19 g).

$^1$H-NMR (CDCl$_3$) δ ppm: 1.19 (3H, t, J=7.6 Hz), 1.84 (3H, s), 2.02 (3H, s), 2.05 (3H, s), 2.09 (3H, s), 2.59 (2H, q, J=7.6 Hz), 3.59 (2H, brs), 3.70–3.90 (3H, m), 4.18 (1H, dd, J=2.5, 12.2 Hz), 4.28 (1H, dd, J=5.3, 12.2 Hz), 5.04 (1H, d, J=7.5 Hz), 5.10–5.35 (3H, m), 6.34 (1H, dd, J=2.1, 8.0 Hz), 6.42 (1H, d, J=2.1 Hz), 6.82 (1H, d, J=8.0 Hz), 6.95–7.15 (4H, m)

Reference Example 32

2-(Methoxymethyloxy)-4,6-dimethylbenzaldehyde

To a solution of 2-hydroxy-4,6-dimethylbenzaldehyde (0.75 g) and N,N-diisopropylethylamine (1.4 mL) in dichloro-methane (20 mL) was added chloromethyl methyl ether (0.57 mL), and the mixture was stirred at room temperature for 24 hours. Water was added to the reaction mixture, and the mixture was extracted with diethyl ether. The organic layer was washed with brine and dried over anhydrous sodium sulfate, and the solvent was removed under reduced pressure. The residue was purified by column chromatography on silica gel (eluent: hexane/ethyl acetate=20/1) to give 2-(methoxymethyloxy)-4,6-dimethylbenzaldehyde (0.57 g).

$^1$H-NMR (CDCl$_3$) δ ppm: 2.34 (3H, s), 2.55 (3H, s), 3.51 (3H, s), 5.26 (2H, s), 6.65–6.70 (1H, m), 6.85–6.90 (1H, m), 10.61 (1H, s)

Reference Example 33

4'-(3-Benzyloxypropyl)-2-(methoxymethyloxy)-4,6-dimethyl-diphenylmethanol

A Grignard reagent was prepared from 1-(3-benzyloxypropyl)-4-bromobenzene (1.3 g), magnesium (0.11 g), a catalytic amount of iodine and tetrahydrofuran (4.4 mL). To the obtained Grignard reagent solution was added a solution of 2-(methoxy-methyloxy)-4,6-dimethylbenzaldehyde (0.57 g) in tetrahydro-furan (10 mL), and the mixture was stirred for 20 minutes. A saturated aqueous ammonium chloride solution was added to the reaction mixture, and the mixture was extracted with ethyl acetate. The organic layer was washed with water and brine, and dried over anhydrous sodium sulfate, and the solvent was removed under reduce pressure. The residue was purified by column chromatography on silica gel (eluent: hexane/ethyl acetate=4/1) to give 4'-(3-benzyloxypropyl)-2-(methoxy-methyloxy)-4,6-dimethyldiphenylmethanol (1.1 g).

$^1$H-NMR (CDCl$_3$) δ ppm: 1.80–1.95 (2H, m), 2.31 (3H, s), 2.32 (3H, s), 2.60–2.75 (2H, m), 3.12 (3H, s), 3.46 (2H, t, J=6.2 Hz), 3.91 (1H, d, J=10.7 Hz), 4.49 (2H, s), 4.93 (1H, d, J=6.5 Hz), 5.03 (1H, d, J=6.5 Hz), 6.03 (1H, d, J=10, 7 Hz), 6.70–6.75 (1H, m), 6.75–6.80 (1H, m), 7.05–7.10 (2H, m), 7.15–7.20 (2H, m), 7.20–7.40 (5H, m)

Reference Example 34

4'-(3-Hydroxypropyl)-2-(methoxymethyloxy)-4,6-dimethyl-diphenylmethane

To a solution of 4'-(3-benzyloxypropyl)-2-(methoxy-methyloxy)-4,6-dimethyldiphenylmethanol (1.1 g) in ethanol (27 mL) was added 10% palladium-carbon powder (0.46 g), and the mixture was stirred under a hydrogen atmosphere at room temperature for 17 hours. An insoluble material was removed by filtration, and the solvent of the filtrate was removed under reduced pressure to give 4'-(3-hydroxypropyl)-2-(methoxy-methyloxy)-4,6-dimethyldiphenylmethane (0.85 g).

$^1$H-NMR (CDCl$_3$) δ ppm: 1.80–1.90 (2H, m), 2.20 (3H, s), 2.30 (3H, s), 2.60–2.70 (2H, m), 3.36 (3H, s), 3.60–3.70 (2H, m), 4.00 (2H, s), 5.13 (2H, s), 6.65–6.70 (1H, m), 6.75–6.85 (1H, m), 7.00–7.10 (4H, m)

Reference Example 35

4'-(3-Benzoyloxypropyl)-2-(methoxymethyloxy)-4,6-dimethyl-diphenylmethane

To a solution of 4'-(3-hydroxypropyl)-2-(methoxy-methyloxy)-4,6-dimethyl-diphenylmethane (0.85 g), triethylamine (0.49 mL) and 4-(dimethylamino)pyridine (0.033 g) in dichloromethane (14 mL) was added benzyl chloride (0.38 mL), and the mixture was stirred at room temperature for 18 hours. Water was added to the reaction mixture, and the mixture was extracted with ethyl acetate. The organic layer was washed with brine and dried over anhydrous sodium sulfate, and the solvent was removed under reduced pressure. The residue was purified by column chromatography on silica gel (eluent: hexane/ethyl acetate=20/1) to give 4'-(3-benzoyloxypropyl)-2-(methoxymethyloxy)-4,6-dimethyl-diphenylmethane (1.1 g).

$^1$H-NMR (CDCl$_3$) δ ppm: 2.00–2.10 (2H, m), 2.20 (3H, s), 2.30 (3H, s), 2.65–2.75 (2H, m), 3.36 (3H, s), 4.00 (2H, s), 4.25–4.35 (2H, m), 5.13 (2H, s), 6.65–6.70 (1H, m), 6.75–6.85 (1H, m), 7.00–7.10 (4H, m), 7.40–7.50 (2H, m), 7.50–7.60 (1H, m), 8.00–8.10 (2H, m)

Example 11

2-[4-(3-Benzoyloxypropyl)benzyl]-3,5-dimethylphenol

To a solution of 4'-(3-benzoyloxypropyl)-2-(methoxymethyloxy)-4,6-dimethyldiphenylmethane (1.1 g) in methanol (13 mL) was added p-toluenesulfonic acid monohydrate (0.096 g), and the mixture was stirred at 60° C. for 4 hours. The reaction mixture was concentrated under reduced pressure, and the residue was purified by column chromatography on silica gel (eluent: hexane/ethyl acetate=6/1) to give 2-[4-(3-benzoyloxypropyl)-benzyl]-3,5-dimethylphenol (0.89 g).

$^1$H-NMR (CDCl$_3$) δ ppm: 2.00–2.10 (2H, m), 2.23 (3H, s), 2.26 (3H, s), 2.65–2.80 (2H, m), 3.98 (2H, s), 4.25–4.35 (2H, m), 4.53 (1H, s), 6.45–6.55 (1H, m), 6.60–6.70 (1H, m), 7.00–7.15 (4H, m), 7.40–7.50 (2H, m), 7.50–7.60 (1H, m), 8.00–8.10 (2H, m)

Example 36

4'-(2-Benzyloxyethyl)-2-(methoxymethyloxy)-4,6-dimethyl-diphenylmethanol

The title compound was prepared in a similar manner to that described in Reference Example 33 using 1-(2-benzyloxyethyl)-4-bromobenzene instead of 1-(3-benzyloxypropyl)-4-bromobenzene.

$^1$H-NMR (CDCl$_3$) δ ppm: 2.30 (3H, s), 2.32 (3H, s), 2.89 (2H, t, J=7.3 Hz), 3.13 (3H, s), 3.64 (2H, t, J=7.3 Hz), 3.89 (1H, d, J=10.7 Hz), 4.50 (2H, s), 4.93 (1H, d, J=6.6 Hz), 5.02 (1H, d, J=6.6 Hz), 6.03 (1H, d, J=10.7 Hz), 6.70–6.75 (1H, m), 6.75–6.80 (1H, m), 7.10–7.35 (9H, m)

Reference Example 37

4'-(2-hydroxyethyl)-2-(methoxymethyloxy)-4,6-dimethyl-diphenylmethane

The title compound was prepared in a similar manner to that described in Reference Example 34 using 4'-(2-benzyloxyethyl)-2-(methoxymethyloxy)-4,6-dimetyldiphenyl-methanol instead of 4'-(3-benzyloxypropyl)-2-(methoxymethyloxy)-4,6-dimethyldiphenylmethanol.

$^1$H-NMR (CDCl$_3$) δ ppm: 1.31 (1H, t, J=5.9 Hz), 2.20 (3H, s), 2.30 (3H, s), 2.80 (2H, t, J=6.5 Hz), 3.37 (3H, s), 3.75–3.85 (2H, m), 4.01 (2H, s), 5.13 (2H, s), 6.65–6.70 (1H, m), 6.75–6.85 (1H, m), 7.05–7.10 (4H, m)

Reference Example 38

4'-(2-Benzoyloxyethyl)-2-(methoxymethyloxy)-4,6-dimethyl-diphenylmethane

The title compound was prepared in a similar manner to that described in Reference Example 35 using 4'-(2-hydroxy-ethyl)-2-(methoxymethyloxy)-4,6-dimetyldiphenylmethane instead of 4'-(3-hydroxypropyl)-2-(methoxymethyloxy)-4,6-dimethyldiphenylmethane.

$^1$H-NMR (CDCl$_3$) δ ppm: 2.19 (3H, s), 2.30 (3H, s), 3.01 (2H, t, J=7.0 Hz), 3.33 (3H, s), 4.01 (2H, s), 4.47 (2H, t, J=7.0 Hz), 5.11 (2H, s), 6.65–6.70 (1H, m), 6.75–6.85 (1H, m), 7.00–7.10 (2H, m), 7.10–7.15 (2H, m), 7.35–7.45 (2H, m), 7.50–7.60 (1H, m), 7.95–8.05 (2H, m)

Example 12

2-[4-(2-Benzoyloxyethyl)benzyl]-3,5-dimethylphenol

The title compound was prepared in a similar manner to that described in Example 11 using 4'-(2-benzoyloxyethyl)-2-(methoxymethyloxy)-4,6-dimethyldiphenylmethane instead of 4'-(3-benzoyloxypropyl)-2-(methoxymethyloxy)-4,6-dimethyl-diphenylmethane.

$^1$H-NMR (CDCl$_3$) δ ppm: 2.22 (3H, s), 2.25 (3H, s), 3.02 (2H, t, J=7.0 Hz), 3.99 (2H, s), 4.49 (2H, t, J=7.0 Hz), 4.60 (1H, brs), 6.45–6.55 (1H, m), 6.60–6.65 (1H, m), 7.05–7.20 (4H, m), 7.35–7.45 (2H, m), 7.50–7.60 (1H, m), 7.95–8.05 (2H, m)

Reference Example 39

2-(4-Ethylbenzyl)-5-(methylamino)phenyl 2,3,4,6-tetra-O-acetyl-β-D-glucopyranoside To a solution of 5-benzyloxycarbonylamino-2-(4-ethylbenzyl)phenyl 2,3,4,6-tetra-O-acetyl-β-D-glucopyranoside (0.42 g) and iodomethane (0.067 mL) in tetrahydrofuran (7 mL) was added sodium hydride (60%, 0.034 g) at 0° C. The reaction mixture was warmed to ambient temperature and stirred for another 5 hours. Iodomethane (0.13 mL) and sodium hydride (60%, 0.020 g) were added to the reaction mixture, and the mixture was stirred for additional 1 hour. The reaction mixture was poured into water, and the mixture was extracted with ethyl acetate. The organic layer was washed with water and dried over anhydrous magnesium sulfate, and the solvent was removed under reduced pressure. The residue was purified by column chromatography on aminopropyl silica gel (eluent: hexane/ethyl acetate=2/1) to give 5-(N-benzyloxycarbonyl-N-methyl)amino-2-(4-ethylbenzyl)-phenyl 2,3,4,6-tetra-O-acetyl-β-D-glucopyranoside (0.30 g). To a solution of the obtained 5-(N-benzyloxycarbonyl-N-methyl)-amino-2-(4-ethylbenzyl)phenyl 2,3,4,6-tetra-O-acetyl-β-D-glucopyranoside (0.30 g) in tetrahydrofuran (5 mL) was added 10% palladium-carbon powder (0.060 g), and the mixture was stirred under a hydrogen atmosphere at room temperature for 6 hours. An insoluble material was removed by filtration, and the solvent of the filtrate was removed under reduced pressure. The residue was purified by column chromatography on silica gel (eluent: hexane/ethyl acetate=1/1) to give 2-(4-ethylbenzyl)-5-(methylamino)phenyl 2,3,4,6-tetra-O-acetyl-β-D-glucopyranoside (0.15 g).

$^1$H-NMR (CDCl$_3$) δ ppm: 1.19 (3H, t, J=7.7 Hz), 1.84 (3H, s), 2.02 (3H, s), 2.04 (3H, s), 2.06 (3H, s), 2.58 (2H, q, J=7.7 Hz), 2.81 (3H, s), 3.65 (1H, brs), 3.70–3.95 (3H, m), 4.18 (1H, dd, J=2.5, 12.3 Hz), 4.26 (1H, dd, J=5.0, 12.3 Hz), 5.07 (1H, d, J=7.7 Hz), 5.10–5.20 (1H, m), 5.20–5.35 (2H, m), 6.28 (1H, dd, J=2.3, 8.2 Hz), 6.36 (1H, d, J=2.3 Hz), 6.85 (1H, d, J=8.2 Hz), 7.00–7.10 (4H, m)

Example 13

4-(4-Ethylbenzyl)-3-hydroxybenzamide

To a mixture of methyl 4-(4-ethylbenzyl)-3-hydroxybenzoate (0.20 g) and 28% aqueous ammonia solution (6 mL) in ethanol (3 mL) was added ammonium chloride (0.079 g), and the mixture was stirred in sealed tube at 100° C. for 14 hours. The reaction mixture was concentrated under reduced pressure, water was added to the residue, and the resulting mixture was extracted with ethyl acetate. The organic layer was dried over anhydrous magnesium sulfate, and the solvent was removed under reduced pressure. A mixed solvent of dichloromethane and methanol (10:1) was added to the residue, and an insoluble material was collected by filtration and dried to give 4-(4-ethylbenzyl)-3-hydroxybenzamide (0.065 g).

$^1$H-NMR (DMSO-d$_6$) δ ppm: 1.14 (3H, t, J=7.6 Hz), 2.54 (2H, q, J=7.6 Hz), 3.85 (2H, s), 7.00–7.15 (6H, m), 7.21 (1H, dd, J=1.7, 7.8 Hz), 7.29 (1H, d, J=1.7 Hz), 7.72 (1H, brs), 9.56 (1H, s)

Reference Example 40

5-Carbamoyl-2-(4-ethylbenzyl)phenyl 2,3,4,6-tetra-O-acetyl-β-D-glucopyranoside The title compound was prepared in a similar manner to that described in Reference Example 27 using 4-(4-ethylbenzyl)-3-hydroxybenzamide instead of 5-methoxy-2-{4-[2-(methoxymethyloxy)ethyl]benzyl}phenol.

$^1$H-NMR (CD$_3$OD) δ ppm: 1.19 (3H, t, J=7.6 Hz), 1.85 (3H, s), 1.99 (3H, s), 2.04 (6H, s), 2.56 (2H, q, J=7.6 Hz), 3.80–4.00 (2H, m), 4.00–4.35 (3H, m), 5.05–5.20 (1H, m), 5.20–5.30 (1H, m), 5.30–5.45 (2H, m), 6.95–7.20 (5H, m), 7.40–7.55 (1H, m), 7.55–7.65 (1H, m)

Reference Example 41

2-Hydroxy-4-(methoxymethyloxy)benzaldehyde

To a suspension of 2,4-dihydroxybenzaldehyde (0.83 g) and cesium carbonate (1.7 g) in acetonitrile (30 mL) was added chloromethyl methyl ether (0.55 mL), and the mixture was stirred at room temperature for 30 minutes. Water was added to the reaction mixture, and the mixture was extracted with ethyl acetate. The organic layer was dried over anhydrous sodium sulfate, and the solvent was removed under reduced pressure. The residue was purified by column chromatography on silica gal (eluent: hexane/ethyl acetate=4/1) to give 2-hydroxy-4-(methoxymethyloxy)benzaldehyde (0.84 g).

$^1$H-NMR (CDCl$_3$) δ ppm: 3.48 (3H, s), 5.22 (2H, s), 6.60 (1H, d, J=2.2 Hz), 6.65 (1H, dd, J=2.2, 8.6 Hz), 7.45 (1H, d, J=8.6 Hz), 9.74 (1H, s), 11.37 (1H, s)

Reference Example 42

4'-Ethyl-2-hydroxy-4-(methoxymethyloxy)diphenylmethanol

To a solution of 1-bromo-4-ethylbenzene (0.46 g) in tetrahydrofuran (12 mL) was added tert-butyl lithium (1.45 mol/L pentane solution, 1.9 mL) under an argon atmosphere at −78° C., and the mixture was stirred for 30 minutes. To the reaction mixture was added a solution of 2-hydroxy-4-methoxymethyl-oxybenzaldehyde(0.18 g) in tetrahydrofuran(6 mL). The mixture was warmed to 0° C. and stirred for additional 15 minutes. A saturated aqueous ammonium chloride solution was added to the reaction mixture, and the mixture was extracted with diethyl ether. The organic layer was dried over anhydrous sodium sulfate, and the solvent was removed under reduced pressure. The residue was purified by column chromatography on silica gel (eluent: hexane/ethyl acetate=3/1) to give 4'-ethyl-2-hydroxy-4-(methoxymethyloxy)diphenylmethanol (0.30 g).

$^1$H-NMR (CDCl$_3$) δ ppm: 1.23 (3H, t, J=7.5 Hz), 2.64 (2H, q, J=7.5 Hz), 2.80 (1H, d, J=3.1 Hz), 3.45 (3H, s), 5.12 (2H, s), 5.95 (1H, d, J=3.1 Hz), 6.47 (1H, dd, J=2.5, 8.5 Hz), 6.61 (1H, d, J=2.5 Hz), 6.72 (1H, d, 8,5 Hz), 7.15–7.25 (2H, m), 7.25–7.35 (2H, m), 8.07 (1H, s)

Example 14

2-(4-Ethylbenzyl)-5-(methoxymethyloxy)phenol

To a solution of 4'-ethyl-2-hydroxy-4-(methoxymethyloxy)diphenylmethanol (0.14 g) in ethanol (5 mL) was added 10% palladium-carbon powder (0.058 g), and the mixture was stirred under a hydrogen atmosphere at room temperature for 1 hour. An insoluble material was removed by filtration, and the solvent of the filtrate was removed under reduced pressure. The residue was purified by column chromatography on silica gel (eluent: hexane/ethyl acetate=4/1) to give 2-(4-ethylbenzyl)-5-(methoxymethyloxy)phenol (0.12 g).

$^1$H-NMR (CDCl$_3$) δ ppm: 1.21 (3H, t, J=7.6 Hz), 2.61 (2H, q, J=7.6 Hz), 3.47 (3H, s), 3.90 (2H, s), 4.73 (1H, s), 5.13 (2H, s), 6.53 (1H, d, J=2.2 Hz), 6.58 (1H, dd, J=2.2, 8.1 Hz), 7.02 (1H, d, J=8.1 Hz), 7.10–7.15 (4H, m)

Reference Example 43

2-(4-Ethylbenzyl)-5-(methoxymethyloxy)phenyl 2,3,4,6-tetra-O-acetyl-β-D-glucopyranoside The title compound was prepared in a similar manner to that described in Reference Example 27 using 2-(4-ethylbenzyl)-5-(methoxymethyloxy)phenol instead of 5-methoxy-2-{4-[2-(methoxymethyloxy)ethyl]benzyl}phenol.

$^1$H-NMR (CDCl$_3$) δ ppm: 1.19 (3H, t, J=7.6 Hz), 1.85 (3H, s), 2.02 (3H, s), 2.05 (3H, s), 2.10 (3H, s), 2.59 (2H, q, J=7.6 Hz), 3.46 (3H, s), 3.79 (1H, d, J=15.5 Hz), 3.84 (1H, d, J=15.5 Hz), 3.85–3.95 (1H, m), 4.19 (1H, dd, J=2.3, 12.2 Hz), 4.27 (1H, dd, J=5.5, 12.2 Hz), 5.05–5.25 (4H, m), 5.25–5.40 (2H, m), 6.69 (1H, dd, J=2.4, 8.4 Hz), 6.68 (1H, d, J=2.4 Hz), 6.96 (1H, d, J=8.4 Hz), 7.00–7.15 (4H, m)

Example 15

2-(4-Methoxybenzyl)-3,5-dimethylphenol

To 3,5-dimethylphenol (12 g) were added lithium hydroxide monohydrate (4.2 g) and 4-methoxybenzyl chloride (14 mL) at 85° C., and the mixture was stirred 1.5 hours. The reaction mixture was cooled to ambient temperature and purified by column chromatography on silica gel (eluent: dichloromethane) to give 2-(4-methoxybenzyl)-3,5-dimethylphenol (5.1 g).

$^1$H-NMR (CDCl$_3$) δ ppm: 2.24 (3H, s), 2.26 (3H, s), 3.77 (3H, s), 3.94 (2H, s), 4.53 (1H, s), 6.45–6.55 (1H, m), 6.55–6.65 (1H, m), 6.75–6.85 (2H, m), 7.00–7.10 (2H, m)

Reference Example 44

2-(4-Methoxybenzyl)-3,5-dimethylphenyl 2,3,4,6-tetra-O-acetyl-β-D-glucopyranoside To a solution of 2-(4-methoxybenzyl)-3,5-dimethylphenol (4.0 g) and 2,3,4,6-tetra-O-acetyl-1-O-trichloroacetoimidoyl-α-D-glucopyranose (8.9 g) in dichloromethane (100 mL) was added boron trifluoride diethyl-ether complex (2.5 mL) at 0° C., and the mixture was stirred at room temperature for 1 hour. The reaction mixture was purified by column chromatography on aminopropyl silica gel (eluent: dichloromethane). The solvent was removed under reduced pressure, ethanol was added to the residue, and the resulting crystals were collected by filtration. The obtained crystals were dried under reduced pressure to give 2-(4-methoxybenzyl)-3,5-dimethylphenyl 2,3,4,6-tetra-O-acetyl-β-D-glucopyranoside (7.8 g).

$^1$H-NMR (CDCl$_3$) δ ppm: 1.65 (3H, s), 2.00 (3H, s), 2.04 (3H, s), 2.09 (3H, s), 2.12 (3H, s), 2.30 (3H, s), 3.74 (3H, s), 3.78 (1H, d, J=15.5 Hz), 3.80–3.95 (1H, m), 4.00 (1H, d, J=15.5 Hz), 4.18 (1H, dd, J=2.5, 12.2 Hz), 4.24 (1H, dd, J=5.8, 12.2 Hz), 5.00–5.20 (2H, m), 5.20–5.35 (2H, m), 6.70–6.80 (4H, m), 6.85–7.00 (2H, m)

Example 16

3-Hydroxy-4-(4-methoxybenzyl)benzamide

The title compound was prepared in a similar manner to that described in Example 13 using methyl 3-hydroxy-4-(4-methoxybenzyl)benzoate instead of methyl 4-(4-ethylbenzyl)-3-hydroxybenzoate. Purification was carried out by column chromatography on silica gel (eluent: dichloromethane/methanol=8/1).

$^1$H-NMR (CD$_3$OD) δ ppm: 3.74 (3H, s), 3.89 (2H, s), 6.75–6.85 (2H, m), 7.03 (1H, d, J=7.8 Hz), 7.05–7.15 (2H, m), 7.21 (1H, dd, J=1.6, 7.8 Hz), 7.27 (1H, d, J=1.6 Hz)

Reference Example 45

3-Hydroxy-4-(4-methoxybenzyl)benzonitrile

To a solution of 3-hydroxy-4-(4-methoxybenzyl)benzamide (0.047 g) and triethylamine (0.30 mL) in dichloromethane (1.8 mL) was added trifluoromethanesulfonic anhydride (0.34 mL), and the mixture was stirred at room temperature overnight. Water was added to the reaction mixture, and the mixture was extracted with ethyl acetate. The organic layer was dried over anhydrous sodium sulfate, and the solvent was removed under reduced pressure. The residue was purified by preparative thin layer chromatography on silica gel (eluent: dichloromethane/methanol=9/1) to give 3-hydroxy-4-(4-methoxybenzyl)benzonitrile (0.014 g).

$^1$H-NMR (CDCl$_3$) δ ppm: 3.80 (3H, s), 4.06 (2H, s), 6.80–6.90 (2H, m), 7.05–7.15 (2H, m), 7.25 (1H, d, J=8.0 Hz), 7.66 (1H, dd, J=1.6, 8.0 Hz), 7.76 (1H, d, J=1.6 Hz)

Reference Example 46

5-Cyano-2-(4-methoxybenzyl)phenyl 2,3,4,6-tetra-O-acetyl-β-D-glucopyranoside The title compound was prepared in a similar manner to that described in Reference Example 27 using 3-hydroxy-4-(4-methoxybenzyl)benzonitrile instead of 5-methoxy-2-(4-[2-(methoxymethyloxy)ethyl]benzyl)phenol.

$^1$H-NMR (CDCl$_3$) δ ppm: 1.93 (3H, s), 2.04 (3H, s), 2.07 (3H, s), 2.14 (3H, s), 3.78 (3H, s), 3.87 (2H, s), 3.90–4.00 (1H, m), 4.15–4.30 (2H, m), 5.05–5.20 (2H, m), 5.25–5.45 (2H, m), 6.75–6.90 (2H, m), 6.95–7.10 (2H, m), 7.10–7.20 (1H, m), 7.20–7.35 (2H, m)

Reference Example 47

2-Hydroxy-4,4'-dimethoxydiphenylmethanol

The title compound was prepared in a similar manner to that described in Reference Example 26 using 4-bromoanisole instead of 1-bromo-4-[2-(methoxymethyloxy)ethyl]benzene.

$^1$H-NMR (CDCl$_3$) δ ppm: 2.66 (1H, d, J=3.0 Hz), 3.77 (3H, s), 3.81 (3H, s), 5.95 (1H, d, J=3.0 Hz), 6.36 (1H, dd, J=2.6, 8.5 Hz), 6.49 (1H, d, J=2.6 Hz), 6.69 (1H, d, J=8.5 Hz), 6.85–6.95 (2H, m), 7.25–7.35 (2H, m), 8.10 (1H, s)

Example 17

5-Methoxy-2-(4-methoxybenzyl)phenol

The title compound was prepared in a similar manner to that described in Example 8 using 2-hydroxy-4,4'-dimethoxy-diphenylmethanol instead of 2-hydroxy-4-methoxy-4'-[2-(methoxymethyloxy)ethyl]diphenylmethanol.

$^1$H-NMR (CDCl$_3$) δ ppm: 3.77 (3H, s), 3.78 (3H, s), 3.87 (2H, s), 4.67 (1H, s), 6.39 (1H, d, J=2.5 Hz), 6.46 (1H, dd, J=2.5, 8.3 Hz), 6.75–6.90 (2H, m), 7.01 (1H, d, J=8.3 Hz), 7.05–7.20 (2H, m)

Reference Example 48

5-Methoxy-2-(4-methoxybenzyl)phenyl 2,3,4,6-tetra-O-acetyl-β-D-glucopyranoside The title compound was prepared in a similar manner to that described in Reference Example 27 using 5-methoxy-2-(4-methoxybenzyl)phenol instead of 5-methoxy-2-{4-[2-(methoxymethyloxy)ethyl]benzyl}phenol.

$^1$H-NMR (CDCl$_3$) δ ppm: 1.88 (3H, s), 2.02 (3H, s), 2.05 (3H, s), 2.09 (3H, s), 3.70–3.95 (9H, m), 4.19 (1H, dd, J=2.5, 12.2 Hz), 4.25 (1H, dd, J=5.9, 12.2 Hz), 5.07 (1H, d, J=7.4 Hz), 5.10–5.40 (3H, m), 6.54 (1H, dd, J=2.4, 8.4 Hz), 6.65 (1H, d, J=2.4 Hz), 6.75–6.85 (2H, m), 6.94 (1H, d, J=8.4 Hz), 7.00–7.10 (2H, m)

Reference Example 49

3-Benzyloxy-4-(4-ethylbenzyl)benzyl alcohol

To a solution of methyl 4-(4-ehtylbenzyl)-3-hydroxy-benzoate (1.3 g) in N,N-dimethylformamide (15 mL) were added potassium carbonate (0.79 g) and benzyl bromide (0.62 mL), and the mixture was stirred at room temperature for 13 hours. Water was added to the reaction mixture, and the mixture was extracted with diethyl ether. The organic layer was washed with water and dried over anhydrous magnesium sulfate, and the solvent was removed under reduced pressure. The residue was dissolved in diethyl ether (10 mL). The resulting solution was added to a suspension of lithium aluminium hydride (0.57 g) in diethyl ether (50 mL) at 0° C., and the mixture was heated under reflux for 1.5 hours. The reaction mixture was cooled to 0° C., water (0.60 mL), 15% aqueous sodium hydroxide solution (0.60 mL) and water (1.8 mL) were successively added to the reaction mixture, and the mixture was stirred for 5 minutes. An insoluble material was removed by filtration, and the solvent of the filtrate was removed under reduced pressure. The residue was purified by column chromatography on silica gel (eluent: hexane/ethyl acetate=2/1) to give 3-benzyloxy-4-(4-ethylbenzyl)benzyl alcohol (1.3 g).

$^1$H-NMR (CDCl$_3$) δ ppm: 1.22 (3H, t, J=7.7 Hz), 1.57 (1H, t, J=6.2 Hz), 2.61 (2H, q, J=7.7 Hz), 3.98 (2H, s), 4.65 (2H, d, J=6.2 Hz), 5.07 (2H, s), 6.87 (1H, dd, J=1.1, 7.5 Hz), 6.97 (1H, d, J=1.1 Hz), 7.05–7.15 (5H, m), 7.25–7.40 (5H, m)

Reference Example 50

[3-Benzyloxy-4-(4-ethylbenzyl)phenyl]acetonitrile

To a solution of 3-benzyloxy-4-(4-ethylbenzyl)benzyl alcohol (0.87 g) in dichloromethane (20 mL) were added triethylamine (0.44 mL) and methanesulfonyl chloride (0.22 mL) at 0° C., and the mixture was stirred for 2 hours. To the reaction mixture was added 0.5 mol/L aqueous hydrochloric acid solution, and the mixture was extracted with diethyl ether. The organic layer was washed with water and a saturated aqueous sodium hydrogen carbonate solution, and dried over anhydrous magnesium sulfate, and the solvent was removed under reducer pressure. The residue was dissolved in dimethyl sulfoxide (10 mL). To the solution were added potassium cyanide (0.68 g) and a catalytic amount of sodium iodide, and the resulting mixture was stirred at 80° C. for 12 hours. Water was added to the reaction mixture, and the mixture was extracted with diethyl ether. The organic layer was washed with water and dried over anhydrous magnesium sulfate, and the solvent was removed under reduced pressure. The residue was purified by column chromatography on silica gel (eluent: hexane/ethyl acetate=5/1–3/1) to give [3-benzyloxy-4-(4-ethylbenzyl)phenyl]acetonitrile (0.41 g).

$^1$H-NMR (CDCl$_3$) δ ppm: 1.22 (3H, t, J=7.5 Hz), 2.61 (2H, q, J=7.5 Hz), 3.70 (2H, s), 3.97 (2H, s), 5.07 (2H, s), 6.80–6.90 (2H, m), 7.05–7.15 (5H, m), 7.25–7.45 (5H, m)

Reference Example 51

2-[3-Benzyloxy-4-(4-ethylbenzyl)phenyl]acetamide

To a mixture of [3-benzyloxy-4-(4-ethylbenzyl)-phenyl] acetonitrile (0.41 g) in ethanol (5 mL) and water (10 mL)was added potassium hydroxide (0.68 g), and the mixture was heated under reflux for 4 hours. The reaction mixture was acidified by adding 2 mol/L aqueous hydrochloric acid solution, and the mixture was extracted with diethyl ether. The organic layer was washed with water and dried over anhydrous magnesium sulfate, and the solvent was removed under reduced pressure to give [3-benzyloxy-4-(4-ethylbenzyl)phenyl]acetic acid (0.41 g). To a solution of the obtained [3-benzyloxy-4-(4-ethylbenzyl)-phenyl]acetic acid (0.41 g) in tetrahydrofuran (10 mL) were added pyridine (0.19 mL), di-tert-butyl dicarbonate (0.50 g) and ammonium hydrogen carbonate (0.18 g), and the mixture was stirred at room temperature for 18 hours. To the reaction mixture was added 1 mol/L aqueous hydrochloric acid solution, and the mixture was extracted with ethyl acetate. The organic layer was washed with water and dried over anhydrous magnesium sulfate, and the solvent was removed under reduced pressure. The residue was purified by column chromatography on silica gel (eluent: dichloromethane/methanol=10/1) to give 2-[3-benzyloxy-4-(4-ethylbenzyl)phenyl]acetamide (0.38 g).

$^1$H-NMR (DMSO-d$_6$) δ ppm: 1.14 (3H, t, J=7.5 Hz), 2.53 (2H, q, J=7.5 Hz), 3.25–3.40 (2H, m), 3.85 (2H, s), 5.06 (2H, s), 6.78 (1H, dd, J=1.0, 7.9 Hz), 6.84 (1H, brs), 6.98 (1H, d, J=1.0 Hz), 7.00–7.10 (5H, m), 7.25–7.45 (6H, m)

Reference Example 52

2-[(4-(4-Ethylbenzyl)-3-hydroxyphenyl]acetamide

To a solution of 2-[3-benzyloxy-4-(4-ethylbenzyl)-phenyl]acetamide (0.38 g) in methanol (5 mL) was added 10% palladium-carbon powder (0.075 g), and the mixture was stirred under a hydrogen atmosphere at room temperature for 4 hours. An insoluble material was removed by filtration, and the solvent of the filtrate was removed under reduced pressure. The residue was purified by column chromatography on silica gel (eluent: dichloromethane/methanol=30/1–20/1) to give 2-[4-(4-ethylbenzyl)-3-hydroxyphenyl]acetamide (0.16 g).

$^1$H-NMR (DMSO-d$_6$) δ ppm: 1.13 (3H, t, J=7.6 Hz), 2.53 (2H, q, J=7.6 Hz), 3.22 (2H, s), 3.77 (2H, s), 6.59 (1H, dd, J=1.5, 7.7 Hz), 6.72 (1H, d, J=1.5 Hz), 6.81 (1H, brs), 6.90 (1H, d, J=7.7 Hz), 7.00–7.15 (4H, m), 7.37 (1H, brs), 9.27 (1H, s)

Reference Example 53

5-Carbamoylmethyl-2-(4-ethylbenzyl)phenyl 2,3,4,6-tetra-O-acetyl-β-D-glucopyranoside The title compound was prepared in a similar manner to that described in Reference Example 27 using 2-[4-(4-ethylbenzyl)-3-hydroxyphenyl]acetamide instead of 5-methoxy-2-{4-[2-(methoxymethyloxy)ethyl]benzyl}phenol.

$^1$H-NMR (CDCl$_3$) δ ppm: 1.20 (3H, t, J=7.6 Hz), 1.88 (3H, s), 2.03 (3H, s), 2.06 (3H, s), 2.07 (3H, s), 2.60 (2H, q, J=7.6 Hz), 3.53 (2H, s), 3.80–3.95 (3H, m), 4.15–4.30 (2H, m), 5.13 (1H, d, J=7.1 Hz), 5.15–5.25 (1H, m), 5.25–5.40 (3H, m), 5.48 (1H, brs), 6.91 (1H, dd, J=1.4, 7.9 Hz), 6.97 (1H, d, J=1.4 Hz), 7.00–7.15 (5H, m)

Reference Example 54

2-Hydroxy-4'-methoxy-4-(methoxymethyl)diphenyl-methanol

The title compound was prepared in a similar manner to that described in Reference Example 26 using 4-bromoanisole and 2-hydroxy-4-methoxymethylbenzaldehyde instead of 1-bromo-4-[2-(methoxymethyloxy)ethyl]benzene and 2-hydroxy-4-methoxy-benzaldehyde.

$^1$H-NMR (CDCl$_3$) δ ppm: 2.71 (1H, d, J=3.1 Hz), 3.37 (3H, s), 3.80 (3H, s), 4.39 (2H, s), 5.99 (1H, d, J=3.1 Hz), 6.70–6.85 (2H, m), 6.85–6.95 (3H, m), 7.25–7.35 (2H, m), 7.98 (1H, s)

Example 18

2-(4-Methoxybenzyl)-5-methoxymethylphenol

To a solution of 2-hydroxy-4'-methoxy-4-(methoxy-methyl)diphenylmethanol (0.17 g) in ethanol (11 mL) was added 10% palladium-carbon powder (0.051 g), and the mixture was stirred under a hydrogen atmosphere at room temperature for 30 minutes. An insoluble material was removed by filtration, and the solvent of the filtrate was removed under reduced pressure. The residue was purified by column chromatography on silica gel (eluent: hexane/ethyl acetate=3/1–2/1) to give 2-(4-methoxy-benzyl)-5-methoxymethylphenol (0.082 g).

$^1$H-NMR (CDCl$_3$) δ ppm: 3.38 (3H, s), 3.78 (3H, s), 3.92 (2H, s), 4.39 (2H, s), 4.77 (1H, s), 6.75–6.90 (4H, m), 7.00–7.20 (3H, m)

Reference Example 55

2-(4-Methoxybenzyl)-5-methoxymethylphenyl 2,3,4,6-tetra-O-acetyl-β-D-glucopyranoside The title compound was prepared in a similar manner to that described in Reference Example 27 using 2-(4-methoxy-benzyl)-5-methoxymethylphenol instead of 5-methoxy-2-{4-[2-(methoxymethyloxy)ethyl]benzyl}phenol.

$^1$H-NMR (CDCl$_3$) δ ppm: 1.90 (3H, s), 2.03 (3H, s), 2.05 (3H, s), 2.08 (3H, s), 3.37 (3H, s), 3.77 (3H, s), 3.84 (2H, s), 3.85–3.95 (1H, m), 4.10–4.30 (2H, m), 4.30–4.50 (2H, m), 5.10–5.25 (2H, m), 5.25–5.40 (2H, m), 6.75–6.85 (2H, m), 6.90–7.10 (5H, m)

Reference Example 56

5-Methoxy-2-{4-[2-(methoxymethyloxy)ethyl]benzyl}phenyl β-D-glucopyranoside To a solution of 5-methoxy-2-{4-[2-(methoxymethyl-oxy)ethyl]benzyl}phenyl 2,3,4,6-tetra-O-acetyl-β-D-glucopyranoside (0.13 g) in methanol (8 mL) was added 2 mol/L aqueous sodium hydroxide solution (0.50 mL), and the mixture was stirred at room temperature for 25 minutes. The solvent was removed under reduced pressure, and the residue was purified by preparative thin layer chromatography on silica gel (eluent: dichloromethane/methanol=7/1) to give 5-methoxy-2-{4-[2-(methoxymethyloxy)ethyl]benzyl}phenyl β-D-glucopyranoside (0.053 g).

$^1$H-NMR (CD$_3$OD) δ ppm: 2.81 (2H, t, J=6.9 Hz), 3.24 (3H, s), 3.30–3.55 (4H, m), 3.60–3.75 (3H, m), 3.75 (3H, s), 3.88 (1H, d, J=15.0 Hz), 3.90 (1H, dd, J=2.0, 12.0 Hz), 4.00 (1H, d, J=15.0 Hz), 4.57 (2H, s), 4.85–4.95 (1H, m), 6.50 (1H, dd, J=2.5, 8.3 Hz), 6.79 (1H, d, J=2.5 Hz), 6.93 (1H, d, J=8.3 Hz), 7.05–7.20 (4H, m)

Reference Example 57

5-[2-(Benzyloxy)ethyloxy]-2-(4-ethylbenzyl)phenyl β-D-glucopyranoside

To a suspension of 2-(4-ethylbenzyl)-5-hydroxyphenyl β-D-glucopyranoside (0.039 g) and cesium carbonate (0.098 g) in N,N-dimethylformamide (1 mL) was added (2-bromo-ethyl)benzyl ether (0.025 mL), and the mixture was stirred at 50° C. for 3.5 hours. The reaction mixture was cooled to ambient temperature, water was added to the reaction mixture, and the mixture was extracted with ethyl acetate. The organic layer was dried over anhydrous sodium sulfate, and the solvent was removed under reduced pressure. The residue was purified by preparative thin layer chromatography on silica gel (eluent: dichloromethane/methanol=6/1) to give 5-[2-(benzyloxy)ethyloxy]-2-(4-ethylbenzyl)phenyl β-D-glucopyranoside (0.022 g).

$^1$H-NMR (CD$_3$OD) δ ppm: 1.18 (3H, t, J=7.6 Hz), 2.57 (2H, q, J=7.6 Hz), 3.30–3.55 (4H, m), 3.67 (1H, dd, J=5.4, 12.1 Hz), 3.75–3.85 (2H, m), 3.86 (1H, d, J=15.0 Hz), 3.88 (1H, dd, J=2.0, 12.1 Hz), 3.98 (1H, d, J=15.0 Hz), 4.05–4.15 (2H, m), 4.58 (2H, s), 4.80–4.90 (1H, m), 6.52 (1H, dd, J=2.4, 8.5 Hz), 6.81 (1H, d, J=2.4 Hz), 6.93 (1H, d, J=8.5 Hz), 7.00–7.20 (4H, m), 7.20–7.40 (5H, m)

Example 19

(E)-2-[4-(3-hydroxy-1-prop-1-ene-1-yl)benzyl]phenyl β-D-glucopyranoside

To a suspension of lithium aluminium hydride (0.036 g) in tetrahydrofuran (5 mL) was added (E)-2-[4-(2-ethoxycarbonyl-vinyl)benzyl]phenyl β-D-glucopyranoside (0.035 g) at 0° C., and the mixture was stirred for 1 hour. Ethyl acetate (10 mL) was added to the reaction mixture, and the mixture was stirred for 30 minutes. To the reaction mixture were added water and dilute hydrochloric acid, and the resulting mixture was extracted with ethylacetate. The organic layer was washed with brine and dried over anhydrous magnesium sulfate, and the solvent was removed under reduced pressure to give (E)-2-[4-(3-hydroxy-1-prop-1-ene-1-yl) benzyl]phenyl β-D-glucopyranoside (0.028 g).

$^1$H-NMR (CD$_3$OD) δ ppm: 3.35–3.55 (4H, m), 3.69 (1H, dd, J=5.0, 12.0 Hz), 3.88 (1H, dd, J=1.8, 12.0 Hz), 3.96 (1H, d, J=14.9 Hz), 4.09 (1H, d, J=14.9 Hz), 4.15–4.25 (2H, m), 4.91 (1H, d, J=7.5 Hz), 6.30 (1H, dt, J=5.9, 16.0 Hz), 6.50–6.60 (1H, m), 6.85–7.25 (6H, m), 7.25–7.35 (2H, m)

Example 20

2-(4-Methoxycarbonylbenzyl)phenyl β-D-glucopyranoside

To a solution of 2-(4-methoxycarbonylbenzyl)phenyl 2,3,4,6-tetra-O-acetyl-β-D-glucopyranoside (0.066 g) in methanol (5 mL) was added sodium methoxide (0.006 g), and the mixture was stirred at room temperature for 30 minutes. The reaction mixture was concentrated under reduced pressure, and the residue was purified by column chromatography on silica gel (eluent: ethyl acetate) to give 2-(4-methoxycarbonyl-benzyl)phenyl β-D-glucopyranoside (0.040 g).

$^1$H-NMR (CD$_3$OD) δ ppm: 3.30–3.55 (4H, m), 3.68 (1H, dd, 5.4, 11.9 Hz), 3.85–3.95 (4H, m), 4.05 (1H, d, J=14.8

Hz), 4.19 (1H, d, J=14.8 Hz), 4.91 (1H, d, J=7.2 Hz), 6.90–7.00 (1H, m), 7.05–7.15 (1H, m), 7.15–7.20 (2H, m), 7.30–7.40 (2H, m), 7.85–7.95 (2H, m)

Example 21

2-(4-Allyloxybenzyl)phenyl β-D-glucopyranoside

To a solution of 2-(4-allyloxybenzyl)phenyl 2,3,4,6-tetra-O-acetyl-β-D-glucopyranoside (0.44 g) in methanol (2.5 mL) and tetrahydrofuran (1.5 mL) was added sodium methoxide (28% methanol solution, 0.30 mL), and the mixture was stirred at room temperature for 4 hours. The solvent of the reaction mixture was removed under reduced pressure, and the residue was purified by column chromatography on silica gel (eluent: dichloro-methane/methanol=10/1) to give 2-(4-allyloxybenzyl)phenyl β-D-glucopyranoside (0.23 g).

$^1$H-NMR (CD$_3$OD) δ ppm: 3.30–3.55 (4H, m), 3.69 (1H, dd, J=4.9, 11.9 Hz), 3.88 (1H, dd, J=2.0, 11.9 Hz), 3.92 (1H, d, J=14.8 Hz), 4.03 (1H, d, J=14.8 Hz), 4.45–4.55 (2H, m), 4.91 (1H, d, J=7.4 Hz), 5.15–5.25 (1H, m), 5.30–5.40 (1H, m), 5.95–6.10 (1H, m), 6.75–6.85 (2H, m), 6.85–6.95 (1H, m), 7.00–7.10 (1H, m), 7.10–7.20 (4H, m)

Example 22

2-[4-(2-Benzyloxyethyl)benzyl]phenyl β-D-glucopyranoside

To a solution of 2-[4-(2-benzyloxyethyl)benzyl]phenol (3.2 g) and 1,2,3,4,6-penta-O-acetyl-β-D-glucopyranose (12 g) in toluene (34 mL) and dichloromethane (17 mL) was added boron trifluoride diethyl-ether complex (3.8 mL), and the mixture was stirred at room temperature for 14 hours. A saturated aqueous sodium hydrogen carbonate solution was added to the reaction mixture, and the resulting mixture was extracted with ethyl acetate. The organic layer was washed with a saturated aqueous sodium hydrogen carbonate solution and brine, and dried over anhydrous sodium sulfate, and the solvent was removed under reduced pressure. The residue was dissolved in methanol (50 mL), sodium methoxide (28% methanol solution, 0.39 mL) was added to the solution, and the mixture was stirred at room temperature for 2.5 hours. The solvent of the reaction mixture was removed under reduced pressure, water was added to the residue, and the resulting mixture was extracted with ethylacetate. The organic layer was washed with brine and dried over anhydrous sodium sulfate, and the solvent was removed under reduced pressure. The residue was purified by column chromatography on silica gel (eluent: dichloromethane/methanol=10/1) to give 2-[4-(2-benzyloxyethyl)benzyl]phenyl β-D-glucopyranoside (3.4 g).

$^1$H-NMR (CD$_3$OD) δ ppm: 2.84 (2H, t, J=7.0 Hz), 3.35–3.55 (4H, m), 3.60–3.75 (3H, m), 3.88 (1H, dd, J=2.0, 12.0 Hz), 3.96 (1H, d, J=14.9 Hz), 4.07 (1H, d, J=14.9 Hz), 4.48 (2H, s), 4.91 (1H, d, J=7.4 Hz), 6.85–6.95 (1H, m), 7.00–7.20 (7H, m), 7.20–7.35 (5H, m)

Example 23

2-(4-Carboxybenzyl)phenyl β-D-glucopyranoside

To a solution of 2-[4-(methoxycarbonyl)benzyl]phenyl 2,3,4,6-tetra-O-acetyl-β-D-glucopyranoside (0.050 g) in methanol (1 mL) was added 2 mol/L aqueous sodium hydroxide solution (0.26 mL), and the mixture was stirred at room temperature for 1 hour. The reaction mixture was purified by column chromatography on benzenesulfonylpropyl silica gel (eluent: methanol) to give 2-(4-carboxybenzyl)phenyl β-D-glucopyranoside (0.038 g).

$^1$H-NMR (CD$_3$OD) δ ppm: 3.30–3.55 (4H, m), 3.69 (1H, dd, J=5.1, 12.1 Hz), 3.88 (1H, dd, J=2.0, 12.1 Hz), 4.04 (1H, d, J=14.8 Hz), 4.19 (1H, d, J=14.8 Hz), 4.85–5.00 (1H, m), 6.85–7.00 (1H, m), 7.05–7.15 (1H, m), 7.15–7.20 (2H, m), 7.30–7.40 (2H, m), 7.85–7.95 (2H, m)

Example 24

2-(4-Cyanomethylbenzyl)phenyl β-D-glucopyranoside 2-(4-Cyanomethylbenzyl)phenyl 2,3,4,6-tetra-O-acetyl-β-D-glucopyranoside was prepared in a similar manner to that described in Reference Example 8 using 4-(2-hydroxybenzyl)-phenylacetonitrile instead of methyl 4-(2-hydroxybenzyl)-benzoate. Then the title compound was prepared in a similar manner to that described in Example 2 using 2-(4-cyano-methylbenzyl)phenyl 2,3,4,6-tetra-O-acetyl-β-D-glucopyranoside instead of 2-(4-methoxycarbonylbenzyl) phenyl 2,3,4,6-tetra-O-acetyl-β-D-glucopyranoside.

$^1$H-NMR (CD$_3$OD) δ ppm: 3.35–3.55 (4H, m), 3.67 (1H, dd, J=5.3, 12.1 Hz), 3.82 (2H, s), 3.88 (1H, dd, J=2.1, 12.1 Hz), 3.99 (1H, d, J=14.9 Hz), 4.12 (1H, d, J=14.9 Hz), 4.91 (1H, d, J=7.6 Hz), 6.85–7.00 (1H, m), 7.00–7.10 (1H, m), 7.10–7.20 (2H, m), 7.20–7.30 (4H, m)

Example 25

2-(4-Carbamoylbenzyl)phenyl β-D-glucopyranoside

To a suspension of 4-(2-hydroxybenzyl)benzamide (0.063 g) and 1,2,3,4,6-penta-O-acetyl-β-D-glucopyranose (0.33 g) in toluene (3 mL) was added boron trifluoride diethyl-ether complex (0.11 mL), and the mixture was stirred at room temperature overnight. The reaction mixture was concentrated under reduced pressure, and the residue was purified by column chromatography on silica gel (eluent: hexane/ethyl acetate=4/1) to give 2-(4-carbamoylbenzyl)phenyl 2,3,4,6-tetra-O-acetyl-β-D-glucopyranoside. To a solution of the obtained 2-(4-carbamoylbenzyl)phenyl 2,3,4,6-tetra-O-acetyl-β-D-glucopyranoside in methanol (5 mL) was added sodium methoxide (0.005 g), and the mixture was stirred at room temperature for 30 minutes. The reaction mixture was concentrated under reduced pressure, and the residue was purified by column chromatography on silica gel (eluent: ethyl acetate/ethanol=5/1) to give 2-(4-carbamoylbenzyl) phenyl β-D-glucopyranoside (0.068 g).

$^1$H-NMR (CD$_3$OD) δ ppm: 3.30–3.55 (4H, m), 3.68 (1H, dd, J=5.5, 11.9 Hz), 3.88 (1H, dd, J=2.1, 11.9 Hz), 4.04 (1H, d, J=14.9 Hz), 4.19 (1H, d, J=14.9 Hz), 4.92 (1H, d, J=7.5 Hz), 6.90–7.00 (1H, m), 7.05–7.15 (1H, m), 7.15–7.20 (2H, m), 7.30–7.40 (2H, m), 7.70–7.80 (2H, m)

Example 26

2-[4-(N,N-dimethylamino)benzyl]phenyl β-D-glucopyranoside

To a solution of 2-[4-(N,N-dimethylamino)benzyl]phenyl 2,3,4,6-tetra-O-acetyl-β-D-glucopyranoside (00.10 g) in methanol (2 mL) and tetrahydrofuran (1 mL) was added sodium methoxide (28% methanol solution, 0.007 mL), and the mixture was stirred at room temperature for 70 minutes. The reaction mixture was concentrated under reduced pressure, and the residue was purified by column chromatography on aminopropyl silica gel (eluent: dichloromethane/methanol=8/1) to give 2-[4-(N,N-dimethylamino)benzyl]phenyl β-D-glucopyranoside (0.069 g).

$^1$H-NMR (CD$_3$OD) δ ppm: 2.85 (6H, s), 3.35–3.55 (4H, m), 3.69 (1H, dd, J=5.2, 12.0 Hz), 3.88 (1H, dd, J=1.9, 12.0 Hz), 3.89 (1H, d, J=15.0 Hz), 3.98 (1H, d, J=15.0 Hz), 4.90 (1H, d, J=7.6 Hz), 6.65–6.75 (2H, m), 6.85–6.95 (1H, m), 7.00–7.05 (1H, m), 7.05–7.10 (2H, m), 7.10–7.15 (2H, m)

Example 27

2-[(4-Benzyloxy)benzyl]phenyl β-D-glucopyranoside

The title compound was prepared in a similar manner to that described in Example 21 using 2-[4-(benzyloxy)benzyl]phenyl 2,3,4,6-tetra-O-acetyl-β-D-glucopyranoside instead of 2-(4-allyloxybenzyl)phenyl 2,3,4,6-tetra-O-acetyl-β-D-glucopyranoside.

$^1$H-NMR (CD$_3$OD) δ ppm: 3.35–3.55 (4H, m), 3.69 (1H, dd, J=5.0, 12.0 Hz), 3.88 (1H, dd, J=2.0, 12.0 Hz), 3.92 (1H, d, J=14.8 Hz), 4.03 (1H, d, J=14.8 Hz), 4.91 (1H, d, J=7.3 Hz), 5.03 (2H, s), 6.80–6.95 (3H, m), 7.00–7.10 (1H, m), 7.10–7.20 (4H, m), 7.25–7.45 (5H, m)

Example 28

2-[4-(2-Hydroxyethyl)benzyl]-5-methoxyphenyl β-D-glucopyranoside

To a solution of 5-methoxy-2-{4-[2-(methoxymethyloxy)ethyl]benzyl}phenyl β-D-glucopyranoside (0.053 g) in methanol (2.3 mL) was added p-toluenesulfonic acid monohydrate (0.032 g), and the mixture was stirred at 50° C. for 3 hours. The reaction mixture was cooled to ambient temperature, triethylamine (0.5 mL) was added to the reaction mixture, and the solvent was removed under reduced pressure. The residue was purified by preparative thin layer chromatography on silica gel (eluent: dichloromethane/methanol=6/1) to give 2-[4-(2-hydroxyethyl)benzyl]-5-methoxyphenyl β-D-glucopyranoside (0.023 g).

$^1$H-NMR (CD$_3$OD) δ ppm: 2.76 (2H, t, J=7.0 Hz), 3.30–3.55 (4H, m), 3.60–3.75 (3H, m), 3.75 (3H, s), 3.87 (1H, d, J=15.0 Hz), 3.89 (1H, dd, J=1.9, 12.2 Hz), 3.99 (1H, d, J=15.0 Hz), 4.85–4.95 (1H, m), 6.50 (1H, dd, J=2.5, 8.3 Hz), 6.78 (1H, d, J=2.5 Hz), 6.94 (1H, d, J=8.3 Hz), 7.05–7.20 (4H, m)

Example 29

5-Amino-2-(4-ethylbenzyl)phenyl β-D-glucopyranoside

To a solution of 5-amino-2-(4-ethylbenzyl)phenyl 2,3,4,6-tetra-O-acetyl-β-D-glucopyranoside (0.19 g) in methanol (3.5 mL) was added sodium methoxide (28% methanol solution, 0.064 mL), and the mixture was stirred at room temperature for 50 minutes. The reaction mixture was concentrated under reduced pressure, and water was added to the residue. The resulting precipitated crystals were collected by filtration, washed with water and dried under reduced pressure to give 5-amino-2-(4-ethylbenzyl)phenyl β-D-glucopyranoside (0.12 g).

$^1$H-NMR (CD$_3$OD) δ ppm: 1.18 (3H, t, J=7.7 Hz), 2.57 (2H, q, J=7.7 Hz), 3.30–3.50 (4H, m), 3.69 (1H, dd, J=5.4, 12.0 Hz), 3.81 (1H, d, J=15.0 Hz), 3.90 (1H, dd, J=2.1, 12.0 Hz), 3.92 (1H, d, J=15.0 Hz), 4.80–4.95 (1H, m), 6.33 (1H, dd, J=2.2, 8.1 Hz), 6.59 (1H, d, J=2.2 Hz), 6.78 (1H, d, J=8.1 Hz), 7.00–7.15 (4H, m)

Example 30

2-[4-(3-Hydroxypropyl)benzyl]-3,5-dimethylphenyl β-D-glucopyranoside

To a solution of 2-[4-(3-benzoyloxypropyl)benzyl]-3,5-dimethylphenol (0.72 g) and 1,2,3,4,6-panta-O-acetyl-β-D-glucopyranose (2.3 g) in toluene (7 mL) and dichloromethane (3 mL) was added boron trifluoride-diethyl ether complex (0.73 mL), and the mixture was stirred at room temperature for 10 hours. Ethyl acetate and a saturated aqueous sodium hydrogen carbonate were added to the reaction mixture, and the organic layer was separated. The organic layer was washed with brine and dried over anhydrous sodium sulfate, and the solvent was removed under reduced pressure. The residue was dissolved in methanol (6 mL) and tetrahydrofuran (4 mL). To the solution was added sodium methoxide (28% methanol solution, 0.19 m), and the mixture was stirred at 30° C. for 7.5 hours. Ethyl acetate and water were added to the reaction mixture, and the organic layer was separated. The organic layer was washed with brine and dried over anhydrous sodium sulfate, and the solvent was removed under reduced pressure. The residue was dissolved in methanol (10 mL), sodium methoxide (28% methanol solution, 0.075 mL) was added to the solution, and the mixture was stirred at 30° C. for 14 hours. The reaction mixture was purified by column chromatography on silica gel (eluent: dichloromethane/methanol=8/1). The solvent was removed under reduced pressure, diethyl ether was added to the residue, and the resulting precipitates were collected by filtration. The obtained solid was washed with diethyl ether and dried under reduced pressure to give 2-[4-(3-hydroxypropyl)-benzyl]-3,5-dimethylphenyl β-D-glucopyranoside (0.58 g).

$^1$H-NMR (CD$_3$OD) δ ppm: 1.70–1.85 (2H, m), 2.13 (3H, s), 2.27 (3H, s), 2.55–2.65 (2H, m), 3.30–3.45 (4H, m), 3.45–3.60 (2H, m), 3.68 (1H, dd, J=5.3, 11.9 Hz), 3.87 (1H, dd, J=2.3, 11.9 Hz), 3.95 (1H, d, J=15.5 Hz), 4.15 (1H, d, J=15.5 Hz), 4.80–4.90 (1H, m), 6.65–6.70 (1H, m), 6.85–6.95 (1H, m), 6.95–7.10 (4H, m)

Example 31

2-[4-(2-Hydroxyethyl)benzyl]-3,5-dimethylphenyl β-D-glucopyranoside

The title compound was prepared in a similar manner to that described in Example 30 using 2-[4-(2-benzoyloxyethyl)benzyl]-3,5-dimethylphenol instead of 2-[4-(3-benzoyloxypropyl)-3,5-dimethylphenol.

$^1$H-NMR (CD$_3$OD) δ ppm: 2.13 (3H, s), 2.27 (3H, s), 2.74 (2H, t, J=7.0 Hz), 3.30–3.45 (4H, m), 3.60–3.75 (3H, m), 3.86 (1H, dd, J=2.3, 11.9 Hz), 3.95 (1H, d, J=15.4 Hz), 4.16 (1H, d, J=15.4 Hz), 4.80–4.90 (1H, m), 6.65–6.70 (1H, m), 6.85–6.95 (1H, m), 7.00–7.10 (4H, m)

Example 32

2-(4-Ethylbenzyl)-5-methylaminophenyl β-D-glucopyranoside

The title compound was prepared in a similar manner to that described in Example 29 using 2-(4-ethylbenzyl)-5- methyl-aminophenyl 2,3,4,6-tetra-O-acetyl-β-D-glucopyranoside instead of 5-amino-2-(4-ethylbenzyl)phenyl 2,3,4,6-tetra-O-acetyl-β-D-glucopyranoside $^1$H-NMR (CD$_3$OD) δ ppm: 1.18 (3H, t, J=7.6 Hz), 2.57 (2H, q, J=7.6 Hz), 2.73 (3H, s), 3.30–3.55 (4H, m), 3.68 (1H, dd, J=5.7, 12.1 Hz), 3.75–4.00 (3H, m), 4.80–4.90 (1H, m), 6.25 (1H, dd, J=2.2, 8.2 Hz), 6.51 (1H, d, J=2.2 Hz), 6.81 (1H, d, J=8.2 Hz), 7.00–7.15 (4H, m)

Example 33

5-Carbamoyl-2-(4-ethylbenzyl)phenyl β-D-glucopyranoside

To a solution of 5-carbamoyl-2-(4-ethylbenzyl)phenyl 2,3,4,6-tetra-O-acetyl-β-D-glucopyranoside (0.13 g) in methanol (3 mL) was added sodium methoxide (28% methanol solution, 0.043 mL), and the mixture was stirred at room temperature for 30 minutes. The reaction mixture was purified by column chromatography on benzenesulfonylpropyl silica gel (eluent: methanol). Diethyl ether was added to the obtained compound, and the resulting precipitated solid was collected by filtration and dried under reduced pressure to give 5-carbamoyl-2-(4-ethyl-benzyl)phenyl β-D-glucopyranoside (0.079 g).

$^1$H-NMR (CD$_3$OD) δ ppm: 1.19 (3H, t, J=7.6 Hz), 2.59 (2H, q, J=7.6 Hz), 3.30–3.60 (4H, m), 3.70 (1H, dd, J=7.2, 12.1 Hz), 3.91 (1H, dd, J=2.2, 12.1 Hz), 4.00 (1H, d, J=15.0 Hz), 4.10 (1H, d, J=15.0 Hz), 5.01 (1H, d, J=7.4 Hz), 7.05–7.20 (5H, m), 7.44 (1H, dd, J=1.7, 7.9 Hz), 7.64 (1H, d, J=1.7 Hz)

Example 34

2-(4-Ethylbenzyl)-5-(methoxymethyloxy)phenyl β-D-glucopyranoside

The title compound was prepared in a similar manner to that described in Reference Example 56 using 2-(4-ethylbenzyl)-5-(methoxymethyloxy)phenyl 2,3,4,6-tetra-O-acetyl-β-D-glucopyranoside instead of 5-methoxy-2-{4-[2-(methoxy-methyloxy)ethyl]benzyl}phenyl 2,3,4,6-tetra-O-acetyl-β-D-glucopyranoside.

$^1$H-NMR (CD$_3$OD) δ ppm: 1.19 (3H, t, J=7.6 Hz), 2.57 (2H, q, J=7.6 Hz), 3.35–3.55 (7H, m), 3.69 (1H, dd, J=5.0, 12.2 Hz), 3.80–3.95 (2H, m), 3.98 (1H, d, J=15.3 Hz), 4.80–4.95 (1H, m), 5.05–5.20 (2H, m), 6.61 (1H, dd, J=2.4, 8.4 Hz), 6.89 (1H, d, J=2.4 Hz), 6.94 (1H, d, J=8.4 Hz), 7.00–7.20 (4H, m)

Example 35

2-(4-Ethylbenzyl)-5-hydroxyphenyl β-D-glucopyranoside

The title compound was prepared in a similar manner to that described in Example 28 using 2-(4-ethylbenzyl)-5-(methoxymethyloxy)phenyl β-D-glucopyranoside instead of 5-methoxy-2-{4-[2-(methoxymethyloxy)ethyl]benzyl}phenyl β-D-glucopyranoside.

$^1$H-NMR (CD$_3$OD) δ ppm: 1.18 (3H, t, J=7.6 Hz), 2.57 (2H, q, J=7.6 Hz), 3.35–3.55 (4H, m), 3.65–3.75 (1H, m), 3.83 (1H, d, J=15.1 Hz), 3.85–3.95 (1H, m), 3.94 (1H, d, J=15.1 Hz), 4.80–4.90 (1H, m), 6.37 (1H, dd, J=2.4, 8.2 Hz), 6.64 (1H, d, J=2.4 Hz), 6.84 (1H, d, J=8.2 Hz), 7.00–7.15 (4H, m)

Example 36

2-(4-Ethylbenzyl)-5-(2-hydroxyethyloxy)phenyl β-D-glucopyranoside

To a solution of 5-[2-(benzyloxy)ethyloxy]-2-(4-ethylbenzyl)phenyl β-D-glucopyranoside (0.022 g) in ethanol (1 mL) was added 10% palladium-carbon powder (0.0082 g), and the mixture was stirred under a hydrogen atmosphere at room temperature for 1 hour. An insoluble material was removed by filtration, and the solvent of the filtrate was removed under reduced pressure. The residue was purified by preparative thin layer chromatography on silica gel (eluent: dichloromethane/methanol=6/1) to give 2-(4-ethylbenzyl)-5-(2-hydroxy-ethyloxy)phenyl β-D-glucopyranoside (0.013 g).

$^1$H-NMR (CD$_3$OD) δ ppm: 1.18 (3H, t, J=7.6 Hz), 2.57 (2H, q, J=7.6 Hz), 3.30–3.55 (4H, m), 3.68 (1H, dd, J=5.5, 12.1 Hz), 3.80–3.95 (4H, m), 3.95–4.05 (3H, m), 4.85–4.90 (1H, m), 6.53 (1H, dd, J=2.3, 8.4 Hz), 6.81 (1H, d, J=2.3 Hz), 6.93 (1H, d, J=8.4 Hz), 7.00–7.15 (4H, m)

Example 37

2-(4-Methoxybenzyl)-3,5-dimethylphenyl β-D-glucopyranoside

To a suspension of 2-(4-methoxybenzyl)-3,5-dimethylphenyl 2,3,4,6-tetra-O-acetyl-β-D-glucopyranoside (7.4 g) in ethanol (150 mL) was added 2 mol/L aqueous sodium hydroxide solution (65 mL), and the mixture was stirred at room temperature for 2 hours. Water was added to the reaction mixture, and the mixture was extracted with ethyl acetate. The organic layer was washed with brine and dried over anhydrous magnesium sulfate, and the solvent was removed under reduced pressure to give 2-(4-methoxybenzyl)-3,5-dimethylphenyl β-D-glucopyranoside (5.2 g).

$^1$H-NMR (CD$_3$OD) δ ppm: 2.13 (3H, s), 2.27 (3H, s), 3.30–3.50 (4H, m), 3.60–3.75 (4H, m), 3.80–4.00 (2H, m), 4.00–4.20 (1H, m), 4.80–4.90 (1H, m), 6.60–6.80 (3H, m), 6.85–6.95 (1H, m), 7.00–7.10 (2H, m)

Example 38

5-Cyano-2-(4-methoxybenzyl)phenyl β-D-glucopyranoside

The title compound was prepared in a similar manner to that described in Reference Example 74 using 5-cyano-2-(4-methoxybenzyl)phenyl 2,3,4,6-tetra-O-acetyl-β-D-glucopyranoside instead of 5-methoxy-2-{4-[2-(methoxy-methyloxy)ethyl]benzyl}phenyl 2,3,4,6-tetra-O-acetyl-β-D-glucopyranoside.

$^1$H-NMR (CD$_3$OD) δ ppm: 3.30–3.45 (1H, m), 3.45–3.60 (3H, m), 3.69 (1H, dd, J=5.9, 12.2 Hz), 3.75 (3H, s), 3.91 (1H, dd, J=2.2, 12.2 Hz), 3.98 (1H, d, J=15.1 Hz), 4.07 (1H, d, J=15.1 Hz), 4.99 (1H, d, J=7.4 Hz), 6.75–6.85 (2H, m), 7.10–7.20 (2H, m), 7.19 (1H, d, J=7.7 Hz), 7.28 (1H, dd, J=1.4, 7.7 Hz), 7.49 (1H, d, J=1.4 Hz)

Example 39

5-Methoxy-2-(4-methoxybenzyl)phenyl β-D-glucopyranoside

The title compound was prepared in a similar manner to that described in Example 29 using 5-methoxy-2-(4-methoxy-benzyl)phenyl 2,3,4,6-tetra-O-acetyl-β-D-glucopyranoside instead of 5-amino-2-(4-ethylbenzyl)phenyl 2,3,4,6-tetra-O-acetyl-β-D-glucopyranoside ¹H-NMR (CD₃OD) δ ppm: 3.30–3.55 (4H, m), 3.68 (1H, dd, J=5.8, 12.0 Hz), 3.74 (3H, s), 3.75 (3H, s), 3.80–4.00 (3H, m), 4.80–4.95 (1H, m), 6.50 (1H, dd, J=2.4, 8.4 Hz), 6.70–6.85 (3H, m), 6.93 (1H, d, J=8.4 Hz), 7.05–7.20 (2H, m)

Example 40

5-Carbamoylmethyl-2-(4-ethylbenzyl)phenyl β-D-glucopyranoside

The title compound was prepared in a similar manner to that described in Example 33 using 5-carbamoylmethyl-2-(4-ethylbenzyl)phenyl 2,3,4,6-tetra-O-acetyl-β-D-glucopyranoside instead of 5-carbamoyl-2-(4-ethylbenzyl)phenyl 2,3,4,6-tetra-O-acetyl-β-D-glucopyranoside.

¹H-NMR (CD₃OD) δ ppm: 1.18 (3H, t, J=7.5 Hz), 2.57 (2H, q, J=7.5 Hz), 3.30–3.55 (6H, m), 3.69 (1H, dd, J=5.7, 12.2 Hz), 3.90 (1H, dd, J=2.2, 12.2 Hz), 3.92 (1H, d, J=14.6 Hz), 4.03 (1H, d, J=14.6 Hz), 4.93 (1H, d, J=7.6 Hz), 6.87 (1H, dd, J=1.4, 7.6 Hz), 7.00 (1H, d, J=7.6 Hz), 7.00–7.20 (5H, m)

Example 41

5-[3-(Ethoxycarbonyl)propyloxy]-2-(4-ethylbenzyl)phenyl β-D-glucopyranoside

To a suspension of 2-(4-ethylbenzyl)-5-hydroxyphenyl β-D-glucopyranoside (0.051 g) and cesium carbonate (0.13 g) in N,N-dimethylformamide (2 mL) was added ethyl 4-bromobutyrate (0.028 mL), and the mixture was stirred at 50° C. for 1 hour. The reaction mixture was cooled to ambient temperature, water was added to the reaction mixture, and the resulting mixture was extracted with ethyl acetate. The organic layer was dried over anhydrous sodium sulfate, and the solvent was removed under reduced pressure. The residue was purified by preparative thin layer chromatography on silica gel (eluent: dichloromethane/methanol=9/1) to give 5-[3-(ethoxycarbonyl)propyloxy]-2-(4-ethylbenzyl)phenyl β-D-glucopyranoside (0.028 g).

¹H-NMR (CD₃OD) δ ppm: 1.18 (3H, t, J=7.6 Hz), 1.23 (3H, t, J=7.1 Hz), 1.95–2.10 (2H, m), 2.48 (2H, t, J=7.5 Hz), 2.57 (2H, q, J=7.6 Hz), 3.30–3.55 (4H, m), 3.68 (1H, dd, J=5.7, 12.1 Hz), 3.80–4.05 (5H, m), 4.12 (2H, q, J=7.1 Hz), 4.88 (1H, d, J=7.4 Hz), 6.49 (1H, dd, J=2.4, 8.8 Hz), 6.77 (1H, d, J=2.4 Hz), 6.92 (1H, d, J=8.8 Hz), 7.00–7.15 (4H, m)

Example 42

2-(4-Methoxybenzyl)-5-methoxymethylphenyl β-D-glucopyranoside

To a solution of 2-(4-methoxybenzyl)-5-methoxymethylphenyl 2,3,4,6-tetra-O-acetyl-β-D-glucopyranoside (0.14 g) in methanol (3 mL) was added sodium methoxide (28% methanol solution, 0.047 mL), and the mixture was stirred at room temperature for 3 hours. The reaction mixture was purified by column chromatography on benzenesulfonylpropyl silica gel (eluent: methanol) to give 2-(4-methoxybenzyl)-5-methoxymethylphenyl β-D-glucopyranoside (0.084 g).

¹H-NMR (CD₃OD) δ ppm: 3.35 (3H, s), 3.30–3.55 (4H, m), 3.69 (1H, dd, J=5.5, 12.1 Hz), 3.74 (3H, s), 3.80–3.95 (2H, m), 4.01 (1H, d, J=15.0 Hz), 4.35–4.45 (2H, m), 4.92 (1H, d, J=7.4 Hz), 6.75–6.85 (2H, m), 6.90 (1H, dd, J=1.4, 7.7 Hz), 7.02 (1H, d, J=7.7 Hz), 7.10–7.20 (3H, m)

Test Example 1

Assay for Inhibitory Effect on Human SGLT2 Activity

1) Construction of the Plasmid Vector Expressing Human SGLT2

Preparation of the cDNA library for PCR amplification was performed by reverse transcription of a total RNA deprived from human kidney (Ori gene) with oligo dT as the primer, using SUPERSCRIPT Preamplification System (Gibco-BRL:LIFE TECHNOLOGIES). The DNA fragment coding for human SGLT2 was amplified by the PCR reaction, in which the human kidney cDNA library described above was used as the template and the following oligo nucleotides 0702F and 0712R, presented as Sequence Number 1 and 2 respectively, were used as the primers. The amplified DNA fragment was ligated into pCR-Blunt (Invitrogen), a vector for cloning, according to standard method of the kit. The *Escherichia coli* HB101 (Toyobo) was transformed according to usual method and then selection of the transformants was performed on the LB agar medium containing 50 μg/mL of kanamycin. After the plasmid DNA was extracted and purified from the one of the transformants, amplifying of the DNA fragment coding for human SGLT2 was performed by the PCR reaction, in which the following oligo nucleotides 0714F and 0715R, presented as Sequence Number 3 and 4 respectively, were used as the primers. The amplified DNA fragment was digested with restriction enzymes, Xho I and Hind III, and then purified with Wizard Purification System (Promega). This purified DNA fragment was inserted at the corresponding restriction sites of pcDNA3.1 (−) Myc/His-B (Invitrogen), a vector for expressing of fusion protein. The *Escherichia coli* HB101 was transformed according to usual method and then selection of the transformant was performed on the LB agar medium containing 100 μg/mL of ampicillin. After the plasmid DNA was extracted and purified from this transformant, the base sequence of the DNA fragment inserted at the multi-cloning sites of pcDNA3.1 (−) Myc/His-B was analyzed. This clone had a single base substitution (ATC which codes for the isoleucine-433 was substituted by GTC) compared with the human SGLT2 reported by Wells et al (Am. J. Physiol., Vol. 263, pp. 459–465 (1992)). Sequentially, a clone in which valine is substituted for the isoleucine-433 was obtained. This plasmid vector expressing human SGLT2 in which the peptide presented as Sequence Number 5 is fused to the carboxyl terminal alanine residue was designated KL29.

| | |
|---|---|
| Sequence Number 1 | ATGGAGGAGCACACAGAGGC |
| Sequence Number 2 | GGCATAGAAGCCCCAGAGGA |
| Sequence Number 3 | AACCTCGAGATGGAGGAGCACACAGAGGC |
| Sequence Number 4 | AACAAGCTTGGCATAGAAGCCCCAGAGGA |
| Sequence Number 5 | KLGPEQKLISEEDLNSAVDHHHHHH |

2) Preparation of the Cells Expressing Transiently Human SGLT2

KL29, the plasmid coding human SGLT2, was transfected into COS-7 cells (RIKEN CELL BANK RCB0539) by electroporation. Electroporation was performed with GENE PULSER II (Bio-Rad Laboratories) under the condition: 0.290 kV, 975 μF, 2×10$^6$ cells of COS-7 cell and 20 μg of KL29 in 500 μL of OPTI-MEM I medium (Gibco-BRL: LIFE TECHNOLOGIES) in the 0.4 cm type cuvette. After the gene transfer, the cells were harvested by centrifugation and resuspended with OPTI-MEM I medium (1 mL/cuvette). To each well in 96-wells plate, 125 μL of this cell suspension was added. After overnight culture at 37° C. under 5% $CO_2$, 125 μL of DMEM medium which is containing 10% of fetal bovine serum (Sanko Jyunyaku), 100 units/mL sodium penicillin G (Gibco-BRL:LIFE TECHNOLOGIES), 100 μg/mL streptomycin sulfate (Gibco-BRL: LIFE TECHNOLOGIES) was added to each well. After a culture until the following day, these cells were used for the measurement of the inhibitory activity against the uptake of methyl-α-D-glucopyranoside.

3) Measurement of the Inhibitory Activity Against the Uptake of methyl-α-D-glucopyranoside After a test compound was dissolved in dimethyl sulfoxide and diluted with the uptake buffer (a pH 7.4 buffer containing 140 mM sodium chloride, 2 mM potassium chloride, 1 mM calcium chloride, 1 mM magnesium chloride, 5 mM methyl-α-D-glucopyranoside, 10 mM 2-[4-(2-hydroxyethyl)-1-piperazinyl]ethane sulfonic acid and 5 mM tris(hydroxymethyl)aminomethane), each diluent was used as test sample for measurement of the inhibitory activity. After removal of the medium of the COS-7 cells expressing transiently human SGLT2, to each well 200 μL of the pretreatment buffer (a pH 7.4 buffer containing 140 mM choline chloride, 2 mM potassium chloride, 1 mM calcium chloride, 1 mM magnesium chloride, 10 mM 2-[4-(2-hydroxyethyl)-1-piperazinyl]ethane sulfonic acid and 5 mM tris(hydroxy-methyl)aminomethane) was added, and the cells were incubated at 37° C. for 10 minutes. After the pretreatment buffer was removed, 200 μL of the same buffer was added again, and the cells were incubated at 37° C. for 10 minutes. The buffer for measurement was prepared by adding of 7 μL of methyl-α-D-(U-14C)-glucopyranoside (Amersham Pharmacia Biotech) to 525 μL of the prepared test sample. For the control, the buffer for measurement without test compound was prepared. For estimate of the basal uptake in the absence of test compound and sodium, the buffer for measurement of the basal uptake, which contains 140 mM choline chloride in place of sodium chloride, was prepared similarly. After the pretreatment buffer was removed, 75 μL of each buffer for measurement was added to each well, the cells were incubated at 37° C. for 2 hours. After the buffer for measurement was removed, 200 μL of the washing buffer (a pH 7.4 buffer containing 140 mM choline chloride, 2 mM potassium chloride, 1 mM calcium chloride, 1 mM magnesium chloride, 10 mM methyl-α-D-glucopyranoside, 10 mM 2-[4-(2-hydroxyethyl)-1-piperazinyl]ethane sulfonic acid and 5 mM tris (hydroxy-methyl)aminomethane) was added to each well and immediately removed. After two additional washing, the cells were solubilized by addition of 75 μL of 0.2 mol/L sodium hydroxide to each well. After the cell lysates were transferred to the PicoPlate (Packard) and 150 μL of MicroScint-40 (Packard) was added to each well, the radioactivity was measured with microplate scintillation counter Top-Count (Packard). The difference in uptake was obtained as 100% value by subtracting the radioactivity in the basal uptake from that in control and then the concentrations at which 50% of uptake was inhibited ($IC_{50}$ Value) were calculated from the concentration-inhibition curve by least square method. The results are shown in the following Table 1.

TABLE 1

| Test compound | $IC_{50}$ value (nM) |
|---|---|
| Example 19 | 120 |
| Example 29 | 10 |
| Example 30 | 30 |
| Example 31 | 59 |
| Example 37 | 290 |

Test Example 2

Assay for the Facilitatory Effect on Urinary Glucose Excretion

As experimental animals, overnight fasted SD rats (Japan SLC. Inc., male, 7 weeks of age, 180–220 g) were used. Ten mg of a test compound was suspended or dissolved in 300 μL of ethanol and dissolved by adding 1.2 mL of polyethylene glycol 400 and 1.5 mL of saline to prepare a 3.3 mg/mL solution. A portion of this solution was diluted with a mixture (saline:polyethylene glycol400:ethanol =5:4:1) to prepare 3.3, 0.33 and 0.33 mg/mL solution. After body weights of the rats were measured, the solution of test compound was intravenously injected to the tail vein at a dose of 3 mL/kg (10, 1, 0.1 mg/kg). For control, only a mixture (saline:polyethylene glycol 400:ethanol=5:4:1) was intravenously injected to the tail vein at a dose of 3 mL/kg. Immediately after intravenous injection to the tail vein, 200 g/L of aqueous glucose solution was orally administered to the rats at a dose of 10 mL/kg (2 g/kg). The intravenous injection to the tail vein was performed with 26 G injection needle and 1 mL syringe. The oral administration was performed with gastric tube for rat and 2.5 mL syringe. The head count in each group was 3. Collection of urine was performed in metabolic cage after the administration of glucose was finished. The sampling time for collection of urine was 24 hours after the administration of glucose. After the collection of urine was finished, the urine volume was recorded and the urinary glucose concentration was measured. The glucose concentration was measured with a kit for laboratory test: Glucose B-Test WAKO (Wako Pure Chemical Industries, Ltd.). The amount of urinary glucose excretion during 24 hours per 200 g of body weight was calculated from the urine volume, urinary glucose concentration and body weight. The results are shown in the following Table 2.

TABLE 2

| Test compound | Dose (mg/kg) | Amount of Urinary Glucose Excretion (mg/24 hours/200 g body weight) |
|---|---|---|
| Example 37 | 0.1 | 15 |
|  | 1 | 125 |
|  | 10 | 288 |

Test Example 3

Acute Toxicity Test

A mixture (saline:polyethylene glycol 400:ethanol =5:4: 1) was added to a test compound to prepare 30 mg/mL solution. As experimental animals, 5 week old male ICR mice (CLEA JAPAN, INC. 29–35 g, 5 animals in each group), which were fasted for 4 hours, were used. The above solution was subcutaneously administered at a dose of 10 mL/kg (300 mg/kg) to the above experimental animals and then observation for 24 hours was performed. The results are shown in the following Table 3.

TABLE 3

| Test compound | Death number |
|---|---|
| Example 37 | 0/5 |

INDUSTRIAL APPLICABILITY

The glucopyranosyloxybenzylbenzene derivatives represented by the above general formula (I) and pharmaceutically acceptable salts thereof of the present invention have an inhibitory activity in human SGLT2 and exert an excellent hypoglycemic effect by excreting glucose in the urine through preventing the reabsorption of excess glucose at the kidney. Therefore, the present invention can provide agents for the prevention or treatment of a disease associated with hyperglycemia such as diabetes, diabetic complication or obesity by comprising as an active ingredient a glucopyranosyloxy-benzylbenzene derivative represented by the above general formula (I) or a pharmaceutically acceptable salt thereof of the present invention.

In addition, compounds represented by the above general formula (II) of the present invention are important as intermediates for preparing the compounds represented by the above general formula (I) or pharmaceutically acceptable salts thereof, and therefore, the compounds represented by the above general formula (I) and pharmaceutically acceptable salts thereof can be readily prepared by way of these compounds.

SEQUENCE LISTING FREE TEXT

Sequence Number 1:Synthetic DNA primer
Sequence Number 2:Synthetic DNA primer
Sequence Number 3:Synthetic DNA primer
Sequence Number 4:Synthetic DNA primer
Sequence Number 5:Peptide fused to the carboxyl terminal alanine residue of human SGLT2

The invention claimed is:

1. A benzylphenol derivative represented by the general formula:

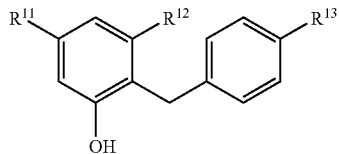

wherein $R^{11}$ represents a hydrogen atom, a protected hydroxy group, a protected amino group, a protected mono(lower alkyl)amino group, a di(lower alkyl)amino group, a carbamoyl group, a lower alkyl group, a lower alkoxy group, a protected hydroxy(lower alkyl) group, a protected hydroxy(lower alkoxy) group, a lower alkoxy-substituted (lower alkyl) group, a lower alkoxy-substituted (lower alkoxy) group, a carbamoyl(lower alkyl) group, a lower alkoxycarbonyl-substituted (lower alkyl) group, a lower alkoxycarbonyl-substituted (lower alkoxy) group, a carboxy-(lower alkyl) group or a carboxy(lower alkoxy) group;

$R^{12}$ represents a hydrogen atom or a lower alkyl group; and $R^{13}$ represents a lower alkyl group, a lower alkoxy group, a lower alkylthio group, a protected hydroxy(lower alkyl) group, a protected hydroxy(lower alkoxy) group, a protected hydroxyl(lower alkylthio) group, a lower alkoxy-substituted (lower alkyl) group, a lower alkoxy-substituted (lower alkoxy) group, a lower alkoxy-substituted (lower alkylthio) group, a lower alkenyloxy group, an aralkyloxy group, a protected hydroxy(lower alkenyl) group, a carboxy group, a lower alkoxycarbonyl group, a cyano group, an aralkyloxy(lower alkyl) group, a carbamoyl group, a carbamoyl(lower alkyl) group, a protected mono(lower alkyl)amino group, a di(lower alkyl)amino group, a lower alkoxycarbonyl-substituted (lower alkyl) group, a lower alkoxycarbonyl-substituted (lower alkoxy) group, a carboxy(lower alkyl) group or a carboxy(lower alkoxy) group; with the proviso that:

$R^{13}$ does not represent a lower alkyl group, a lower alkoxy group, a lower alkylthio group, a protected hydroxy (lower alkyl) group, a protected hydroxy(lower alkoxy) group, a protected hydroxy(lower alkylthio) group, a lower alkoxy-substituted (lower alkyl) group, a lower alkoxy-substituted (lower alkoxy) group or a lower alkoxy-substituted (lower alkylthio) group when $R^{11}$ represents a hydrogen atom or a protected hydroxy (lower alkyl) group $R^{12}$ represents a hydrogen atom, or a salt thereof.

* * * * *